US012566171B2

(12) United States Patent
Swett et al.

(10) Patent No.: US 12,566,171 B2
(45) Date of Patent: Mar. 3, 2026

(54) DETERMINING A VOLUME OF METALLIC SWARF IN A WELLBORE FLUID

(71) Applicant: Saudi Arabian Oil Company, Dhahran (SA)

(72) Inventors: Dwight W. Swett, Cypress, TX (US); Timothy Thiel, Houston, TX (US); Richard Pye, Dhahran (SA); Atallah N. Al-Harbi, Dhahran (SA); Huseyin Rahmi Seren, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 126 days.

(21) Appl. No.: 18/617,341

(22) Filed: Mar. 26, 2024

(65) Prior Publication Data

US 2025/0306003 A1     Oct. 2, 2025

(51) Int. Cl.
*G01N 33/28*          (2006.01)
(52) U.S. Cl.
CPC ..... *G01N 33/2858* (2013.01); *G01N 33/2823* (2013.01)
(58) Field of Classification Search
CPC . G01V 3/00; G01V 3/182; G01V 3/22; G01V 3/24; G01V 3/26; G01V 3/28; G01V 2210/644; G01V 2210/645; E21B 47/008; E21B 49/00; E21B 49/003; E21B 49/005; E21B 49/08; E21B 49/081; E21B 49/0813; E21B 49/0815; E21B 49/082; E21B 49/084; E21B 49/087; E21B 49/0875; E21B 49/088; E21B 49/10; G01N 33/2823; G01N 33/2858; G01N 27/74; G01N 27/76; G01N 29/02; G01N 29/022; G01N 29/028; G01F 1/74; G01F 1/76; G01F 1/8418; G01F 1/8422; G01F 1/845; G01F 1/8459; G01F 1/8468
See application file for complete search history.

(56) References Cited

U.S. PATENT DOCUMENTS

| | | | |
|---|---|---|---|
| 3,498,455 A | 3/1970 | Kirby, III | |
| 9,227,198 B2 | 1/2016 | Branch et al. | |
| 11,635,369 B1 | 4/2023 | Swett | |
| 11,774,289 B2 | 10/2023 | Swett | |

(Continued)

OTHER PUBLICATIONS

U.S. Appl. No. 18/319,294, Swett, filed May 17, 2023.

(Continued)

*Primary Examiner* — David M Schindler
(74) *Attorney, Agent, or Firm* — Fish & Richardson P.C.

(57)          ABSTRACT

A metallic swarf sensor includes a housing configured to couple to a fluid conduit that includes a flowpath for a circulation of a wellbore fluid that includes metallic swarf; a magnetic tine assembly that includes a pair of magnetic tines that extend from the housing and connect through a magnetic flexure; a magnetic assembly at least partially enclosed within the housing and coupled to the magnetic tine assembly; and a piezoelectric actuator at least partially enclosed within the housing and coupled to the magnetic tine assembly. The magnetic assembly is configured to magnetize the magnetic tine assembly. The piezoelectric actuator is configured to resonate the magnetic tine assembly at a variable resonance frequency.

30 Claims, 18 Drawing Sheets

(56) References Cited

U.S. PATENT DOCUMENTS

| 2015/0082873 A1* | 3/2015 | Goodbread | ............ | G01N 9/002 |
| | | | | 73/54.41 |
| 2017/0038491 A1* | 2/2017 | Gonzalez | ................ | E21B 49/08 |
| 2020/0041395 A1* | 2/2020 | Swett | .................... | G01N 9/002 |

OTHER PUBLICATIONS

U.S. Appl. No. 18/471,037, Swett, filed Sep. 20, 2023.
U.S. Appl. No. 18/784,458, Swett et al., filed Jul. 25, 2024.
Anesbug et al., "Field Experience Using Flow Positioned Ditch Magnet Systems—Contribution to Efficient Drilling," Presented at the SPE Offshore Europe Conference & Exhibition, Aberdeen, Scotland, UK, Sep. 2023, Abstract only, 1 page.
Saasen et al., "Removal of Magnetic Metallic Contamination—Improved Drilling Fluid Performance," Prepared for presentation at the SPE Offshore Europe Conference and Exhibition held in Aberdeen, UK, Sep. 3-6, 2019, 9 pages.

* cited by examiner

400

450

700

702

1.48
1.41
1.34
1.26
1.19
1.11
1.04
0.97
0.89
0.82
0.74
0.67
0.6
0.52
0.45
0.37
0.3
0.23
0.15
0.08
0.01 x
y      z

750

754

756

752

Magnetic flux density norm (T)

0.65
0.6
0.55
0.5
0.45
0.4
0.35
0.3
0.25

0    50   100  150  200  250  300  350

Arc length (mm)

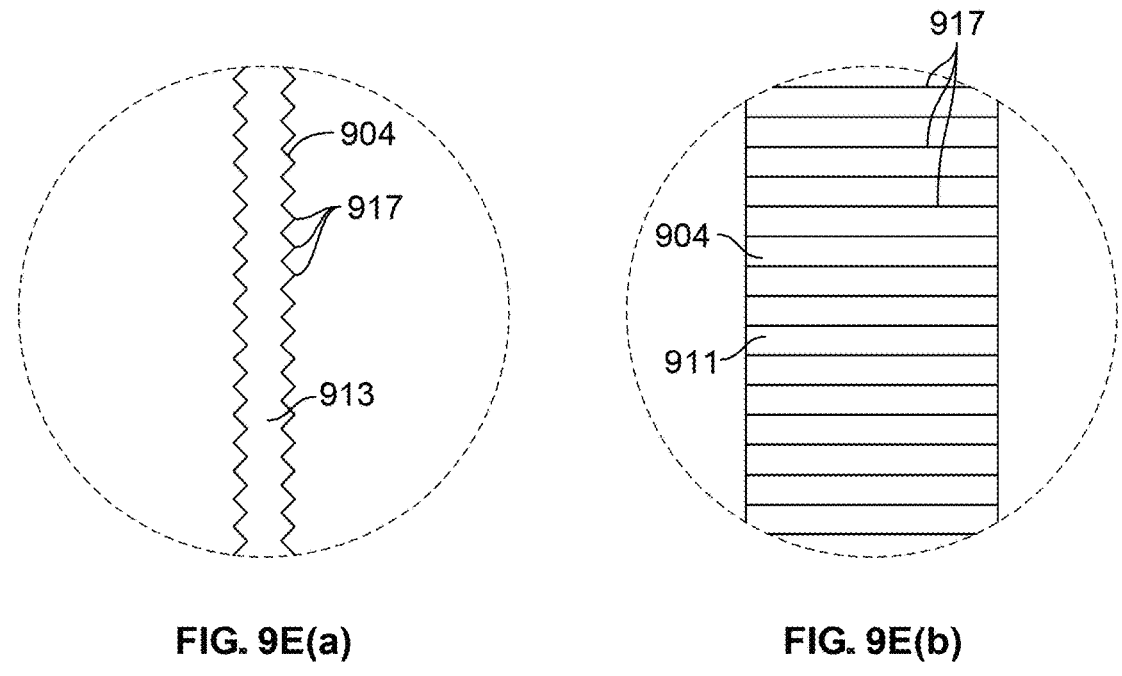
FIG. 9E(a)                FIG. 9E(b)
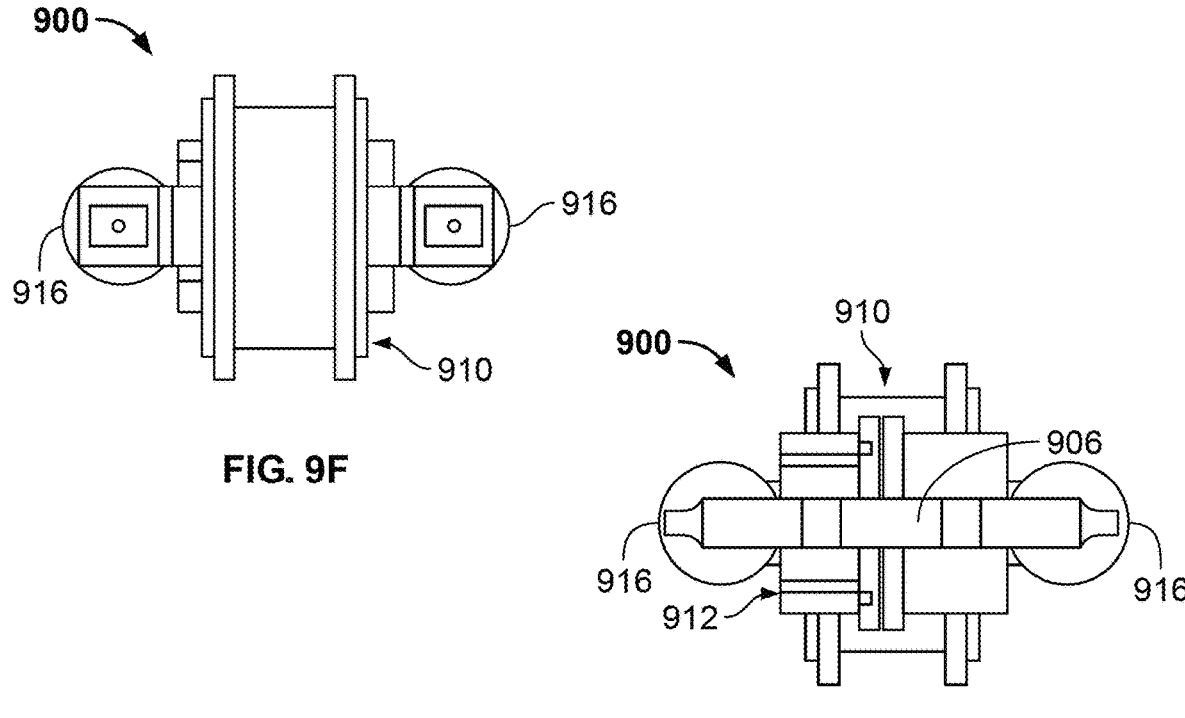
FIG. 9F
FIG. 9G

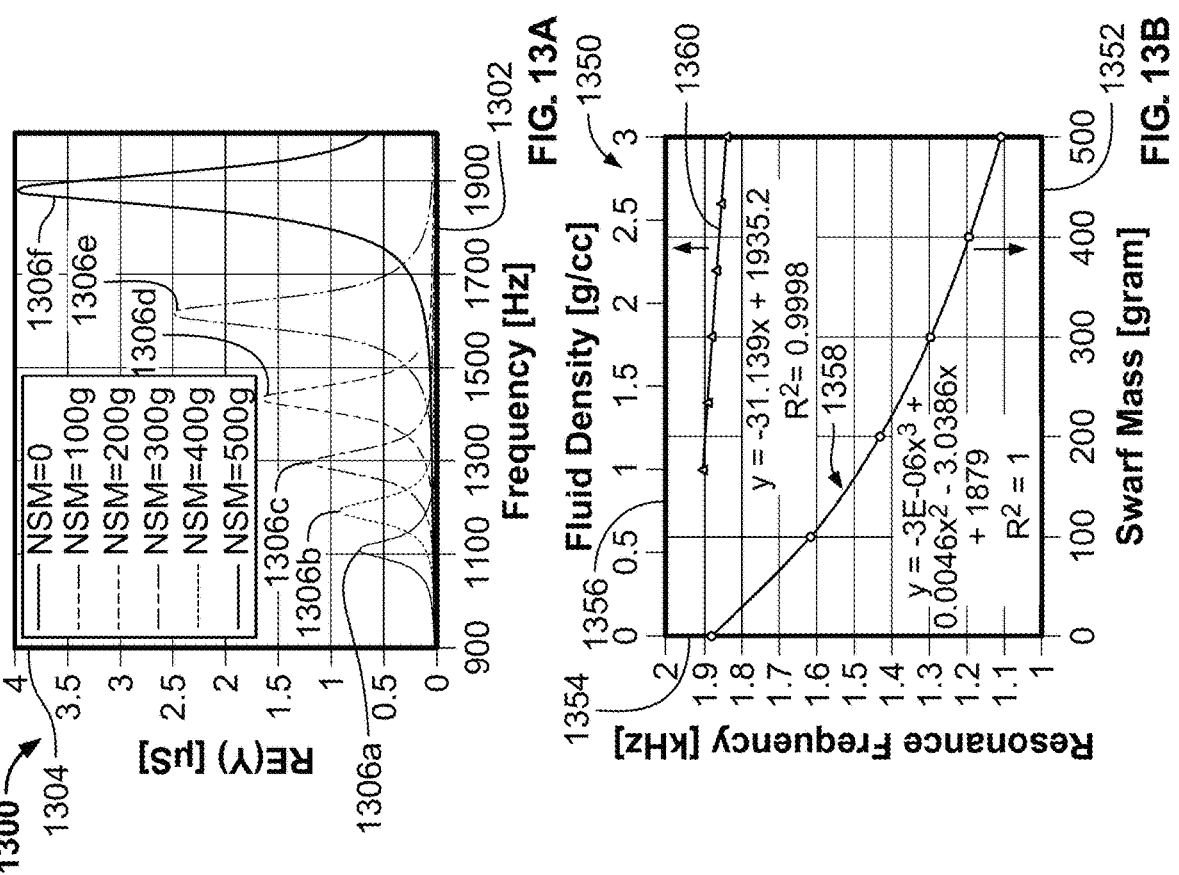
FIG. 13A
FIG. 13B
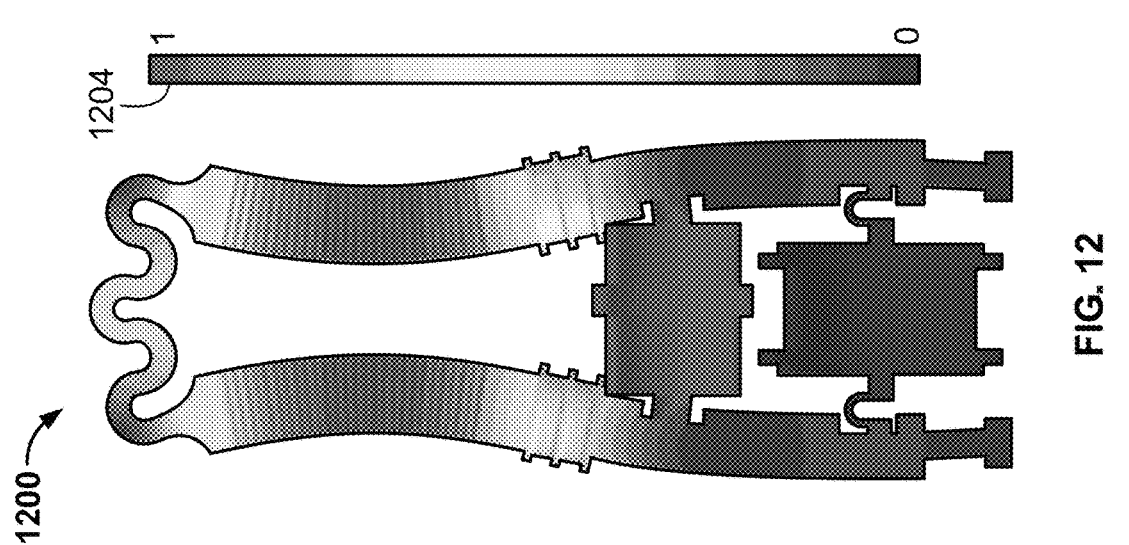
FIG. 12

DETERMINING A VOLUME OF METALLIC SWARF IN A WELLBORE FLUID

TECHNICAL FIELD

The present disclosure describes systems and methods for determining a volume of metallic swarf in a wellbore fluid and, more particularly, determining a volume of metallic swarf generated from sidetrack milling operations in a wellbore fluid.

BACKGROUND

It can be advantageous to accurately measure a volume of metallic swarf (residue) flowing out of a wellbore during sidetrack milling operations to determine if the sidetrack from a whipstock has been successful. The volume of metallic swarf exiting the wellbore is known to be an indicator of the success of these type of downhole milling operations. An accurate measurement of the volume of metallic swarf from a milling operation is known to be a good indicator for (i) proper hole cleaning practices, (ii) estimation of window milling progress and effectiveness (e.g., proper sidetracking will result in greater volume of metal while a premature exit will result in minimal volume of metallic swarf), and (iii) an estimation of the metallic assemblies of various types that may remain in the hole which represent a risk for a stuck-pipe event and or damage to the drilling bit. Also, accurate measurement of metal recovery helps optimize mill design and bottom hole assembly design.

Traditional methods to monitor the volume of metallic swarf exiting the borehole involve intermittently capturing (manually) the metallic swarf on ditch magnets and then weighing each capture to track the total swarf generated during the milling operation. However, owing to the manual nature of this process, as the ditch magnets become loaded with swarf material, the magnetic field deteriorates such that the remaining exposed surfaces of the magnet are unable to capture particles and miss the ensuing swarf in the flowline which simply flows past to the shale shakers which sometimes damages the screens. In the event that the volume of metal flowing back from the wellbore is more than anticipated, this can be an indication of improper tracking in which the mill does not exit the casing properly and simply mills the whipstock instead. Such an improper event holds significant implications for the next downhole assembly to be run, and the volume of metallic swarf represents an early indicator if a kick off from the whipstock has been successful or not.

SUMMARY

In an example implementation, a metallic swarf sensor includes a housing configured to couple to a fluid conduit that includes a flowpath for a circulation of a wellbore fluid that includes metallic swarf; a magnetic tine assembly that includes a pair of magnetic tines that extend from the housing and connect through a magnetic flexure; a magnetic assembly at least partially enclosed within the housing and coupled to the magnetic tine assembly, the magnetic assembly configured to magnetize the magnetic tine assembly; and a piezoelectric actuator at least partially enclosed within the housing and coupled to the magnetic tine assembly, the piezoelectric actuator configured to resonate the magnetic tine assembly at a variable resonance frequency.

In an aspect combinable with the example implementation, the piezoelectric actuator is coupled to the magnetic tine assembly at a first pivot point coupled to a first magnetic tine of the pair of magnetic tines and at a second pivot point coupled to a second magnetic tine of the pair of magnetic tines.

In another aspect combinable with one, some, or all of the previous aspects, the magnetic assembly includes a magnetic core; and an electromagnetic coil wrapped around the magnetic core and electrically coupled to a power source through one or more electrical feedthrough connections.

Another aspect combinable with one, some, or all of the previous aspects includes a controller electrically coupled to the electromagnetic coil.

In another aspect combinable with one, some, or all of the previous aspects, the controller is configured to perform operations including applying a current from the power source to the electromagnetic coil to magnetize the magnetic tine assembly to magnetically attract metallic swarf to the magnetic tine assembly from the wellbore fluid; decoupling the current from the power source to the electromagnetic coil to demagnetize the magnetic tine assembly to cease to magnetically attract metallic swarf to the magnetic tine assembly from the wellbore fluid; and operating the electromagnetic coil to perform a reverse degauss process to clean metallic swarf from the magnetic tine assembly.

In another aspect combinable with one, some, or all of the previous aspects, the current is a first current at a first magnetic polarity.

In another aspect combinable with one, some, or all of the previous aspects, the operation of operating the electromagnetic coil to perform the reverse degauss process to clean metallic swarf from the magnetic tine assembly includes applying a second current at a second magnetic polarity that is reverse from the first magnetic polarity from the power source to the electromagnetic coil to demagnetize the magnetic tine assembly to repel metallic swarf attached to the magnetic tine assembly.

In another aspect combinable with one, some, or all of the previous aspects, the magnetic assembly includes a permanent magnet; and a poling coil wrapped around the permanent magnet and electrically coupled to a power source through one or more electrical feedthrough connections.

Another aspect combinable with one, some, or all of the previous aspects includes a controller electrically coupled to the poling coil and configured to perform operations including applying a current from the power source to the poling coil to depole the permanent magnet and switch a magnetic field generated by the permanent magnet; and based on the switched magnetic field, demagnetizing the magnetic tine assembly to magnetically repel metallic swarf attached to the magnetic tine assembly.

In another aspect combinable with one, some, or all of the previous aspects, the operation of applying the current includes applying a current of sufficient magnitude to overcome an intrinsic coercivity of the permanent magnet.

In another aspect combinable with one, some, or all of the previous aspects, the current of sufficient magnitude is determined by $$i = \left[ \frac{L_{PM}}{N_{turns}} \right] H_{ci},$$

where $L_{PM}$ is an axial dimension of the permanent magnet, i is the current magnitude in the poling coil, $H_{ci}$ is the intrinsic coercivity, and $N_{turns}$ is a total number of turns of the poling coil.

In another aspect combinable with one, some, or all of the previous aspects, each of the pair of magnetic tines includes a blade, and the magnetic flexure includes a sinusoidal shape.

In another aspect combinable with one, some, or all of the previous aspects, the blade includes a plurality of teeth.

In another aspect combinable with one, some, or all of the previous aspects, the magnetic tine assembly includes a magnetic stainless steel alloy.

In another example implementation, a method for managing metallic swarf in a drilling fluid includes circulating a drilling fluid through a flowpath of a fluid conduit that includes at least one metallic swarf sensor coupled to the fluid conduit, the drilling fluid including metallic swarf; energizing a magnetic assembly at least partially enclosed within a housing of the metallic swarf sensor that is coupled to an exterior of the fluid conduit; based on energizing the magnetic assembly, magnetizing a magnetic tine assembly of the metallic swarf sensor that extends into the flowpath from the housing, the magnetic tine assembly including a pair of magnetic tines that extend from the housing and connect through a magnetic flexure; resonating, at a variable resonance frequency, the magnetic tine assembly with a piezoelectric actuator at least partially enclosed within the housing; and magnetically attracting at least a portion of the metallic swarf in the drilling fluid to the magnetized magnetic tine assembly.

An aspect combinable with the example implementation includes resonating the magnetic tine assembly with the piezoelectric actuator through a first pivot point coupled to a first magnetic tine of the pair of magnetic tines and through a second pivot point coupled to a second magnetic tine of the pair of magnetic tines.

In another aspect combinable with one, some, or all of the previous aspects, energizing the magnetic assembly includes providing a current from a power source to an electromagnetic coil wrapped around a magnetic core through one or more electrical feedthrough connections.

Another aspect combinable with one, some, or all of the previous aspects includes magnetizing the magnetic tine assembly by providing the current from the power source to the electromagnetic coil; magnetically attracting metallic swarf from the drilling fluid to the magnetic tine assembly; decoupling the current from the power source to the electromagnetic coil to demagnetize the magnetic tine assembly to cease to magnetically attract metallic swarf to the magnetic tine assembly from the wellbore fluid; and operating the electromagnetic coil to perform a reverse degauss process to clean metallic swarf from the magnetic tine assembly.

In another aspect combinable with one, some, or all of the previous aspects, the current is a first current at a first magnetic polarity.

In another aspect combinable with one, some, or all of the previous aspects, operating the electromagnetic coil to perform the reverse degauss process to clean metallic swarf from the magnetic tine assembly includes providing a second current at a second magnetic polarity that is reverse from the first magnetic polarity from the power source to the electromagnetic coil to demagnetize the magnetic tine assembly to repel metallic swarf attached to the magnetic tine assembly.

In another aspect combinable with one, some, or all of the previous aspects, energizing the magnetic assembly includes generating a magnetic field with a permanent magnet around which is wrapped a poling coil that is electrically coupled to a power source through one or more electrical feedthrough connections.

Another aspect combinable with one, some, or all of the previous aspects includes providing a current from the power source to the poling coil to depole the permanent magnet and switch a magnetic field generated by the permanent magnet; and based on the switched magnetic field, demagnetizing the magnetic tine assembly to magnetically repel metallic swarf attached to the magnetic tine assembly.

In another aspect combinable with one, some, or all of the previous aspects, applying the current includes applying a current of sufficient magnitude to overcome an intrinsic coercivity of the permanent magnet.

In another aspect combinable with one, some, or all of the previous aspects, the current of sufficient magnitude is determined by $$i = \left[\frac{L_{PM}}{N_{turns}}\right] H_{ci},$$

where $L_{PM}$ is an axial dimension of the permanent magnet, i is the current magnitude in the poling coil, $H_{ci}$ is the intrinsic coercivity, and $N_{turns}$ is a total number of turns of the poling coil.

In another aspect combinable with one, some, or all of the previous aspects, each of the pair of magnetic tines includes a blade, and the magnetic flexure includes a sinusoidal shape.

In another aspect combinable with one, some, or all of the previous aspects, the blade includes a plurality of teeth.

In another aspect combinable with one, some, or all of the previous aspects, the magnetic tine assembly includes a magnetic stainless steel alloy.

In another example implementation, a drilling fluid sensor array includes at least a portion of a flow conduit configured to circulate a drilling fluid including metallic swarf from a wellbore; a first metallic swarf sensor coupled to the flow conduit; and a second metallic swarf sensor coupled to the flow conduit. The first metallic swarf sensor includes a first housing coupled to the flow conduit; a first magnetic tine assembly that includes a first pair of magnetic tines that extend from the housing and connect through a first magnetic flexure; a first magnetic assembly at least partially enclosed within the first housing and coupled to the first magnetic tine assembly, the first magnetic assembly configured to magnetize the first magnetic tine assembly; and a first piezoelectric actuator at least partially enclosed within the first housing and coupled to the first magnetic tine assembly, where the first piezoelectric actuator is configured to resonate the first magnetic tine assembly at a variable resonance frequency. The second metallic swarf sensor includes a second housing coupled to the flow conduit; a second magnetic tine assembly that includes a second pair of magnetic tines that extend from the housing and connect through a second magnetic flexure; a second magnetic assembly at least partially enclosed within the second housing and coupled to the second magnetic tine assembly, the second magnetic assembly configured to magnetize the second magnetic tine assembly; and a second piezoelectric actuator at least partially enclosed within the second housing and coupled to the second magnetic tine assembly, where the second piezoelectric actuator is configured to resonate the second magnetic tine assembly at a variable resonance frequency.

In an aspect combinable with the example implementation, the first metallic swarf sensor is coupled to the flow conduit on a first side, and the second metallic swarf sensor is coupled to the flow conduit on a second side opposite the first side.

Another aspect combinable with one, some, or all of the previous aspects includes a third metallic swarf sensor coupled to the flow conduit, and the third metallic swarf sensor includes a third housing coupled to the flow conduit; a third magnetic tine assembly that includes a third pair of magnetic tines that extend from the housing and connect through a third magnetic flexure; a third magnetic assembly at least partially enclosed within the third housing and coupled to the third magnetic tine assembly, the third magnetic assembly configured to magnetize the third magnetic tine assembly; and a third piezoelectric actuator at least partially enclosed within the third housing and coupled to the third magnetic tine assembly, the third piezoelectric actuator configured to resonate the third magnetic tine assembly at a variable resonance frequency.

Another aspect combinable with one, some, or all of the previous aspects includes a fourth metallic swarf sensor coupled to the flow conduit, and the fourth metallic swarf sensor includes a fourth housing coupled to the flow conduit; a fourth magnetic tine assembly that includes a fourth pair of magnetic tines that extend from the housing and connect through a fourth magnetic flexure; a fourth magnetic assembly at least partially enclosed within the fourth housing and coupled to the fourth magnetic tine assembly, the fourth magnetic assembly configured to magnetize the fourth magnetic tine assembly; and a fourth piezoelectric actuator at least partially enclosed within the fourth housing and coupled to the fourth magnetic tine assembly, the fourth piezoelectric actuator configured to resonate the fourth magnetic tine assembly at a variable resonance frequency.

In another aspect combinable with one, some, or all of the previous aspects, the third metallic swarf sensor is coupled to the flow conduit on the first side, and the fourth metallic swarf sensor is coupled to the flow conduit on the second side.

In another aspect combinable with one, some, or all of the previous aspects, each of the first pair of magnetic tines includes a blade, and the first magnetic flexure includes a sinusoidal shape, and each of the second pair of magnetic tines includes a blade, and the second magnetic flexure includes the sinusoidal shape.

In another aspect combinable with one, some, or all of the previous aspects, the blade of each magnetic tine of the first and second pair of magnetic tines includes a flat side angled relative to a direction of flow of the drilling fluid.

Implementations of systems and methods for determining a volume of metallic swarf in a wellbore fluid according to the present disclosure may also include one or more of the following features. For example, implementations according to the present disclosure can provide for techniques to continuously and automatically measure or account for an amount of metallic swarf returned in a drilling fluid from a drilling (for example, sidetrack) operation, thereby providing an indication of the progress and success of the operation.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

FIGS. 9A-9G are schematic diagrams of another example implementation of a metallic swarf sensor according to the present disclosure.

FIG. 12 is a graphic that shows a resonance frequency deformation shape of a metallic swarf sensor according to the present disclosure.

FIGS. 13A and 13B are graphs that illustrate operational characteristics of a metallic swarf sensor according to the present disclosure.

DETAILED DESCRIPTION

The present disclosure describes example implementations of a metallic swarf sensor that includes a mechanical resonator with oscillating tines connected through a tip flexure, intermediate located pivot flexure (electromagnetic or permanent magnet core), and a piezoelectric actuator. The mechanical resonator can be excited through a piezoelectric actuator stack that imparts linear harmonic motion laterally at an end of the tines to sweep an oscillating frequency of the resonator tines to determine resonance frequency of the sensor, including magnetically attached swarf from a wellbore fluid that flows past the tines. The vibrating tine assembly (for example, including the pivot point core and flexure) can be comprised of a magnetic material, such as a magnetic stainless steel metal material (for example, Carpenter Alloy 430F) that is magnetized through the use of an electromagnet (composed of wound wire coil and the core) or permanent magnet. which is connected magnetically to each other through core flexures from each side of the core.

In some aspects, the core flexure connection forms a pivot point that is unsymmetrically positioned vertically between a piezoelectric actuator plane and ends of the tines. The pivot point location can develop an amplification of lateral motion at the resonator tines, which can enhance a sensitivity of the sensor to accumulation of swarf on the surfaces of the tines. The magnetized tines are attractive to ferrous swarf flowing within a wellbore fluid (such as a returned drilling fluid or mud). Thus, references to a metallic swarf sensor in the present disclosure includes reference to a metallic swarf sensor that can collect (on the tines) metallic swarf, at least transiently.

Figure 1A:
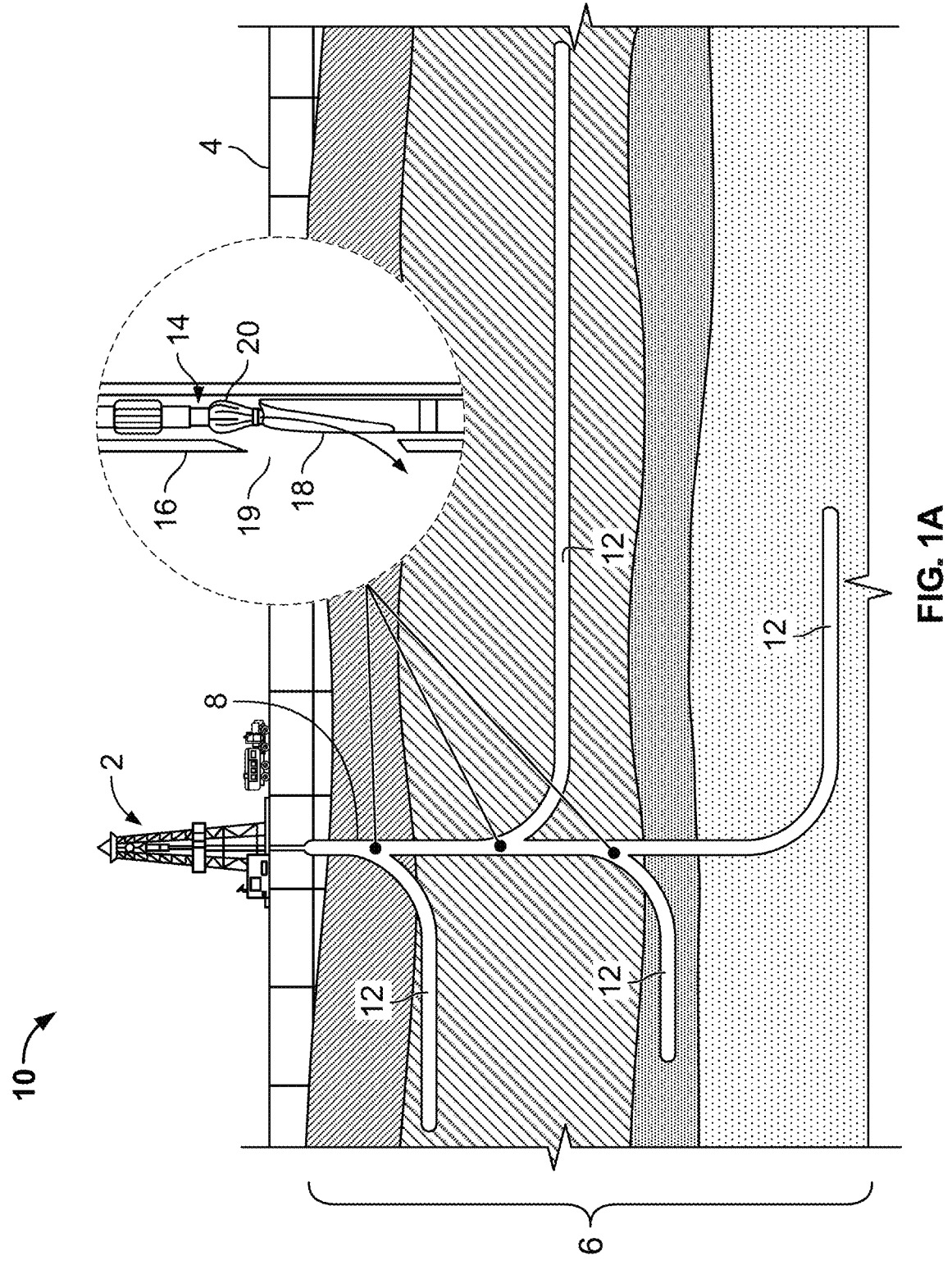
FIG. 1A is a schematic diagram of a drilling operation that can include the generation of metallic swarf according to the present disclosure.

FIG. 1A is a schematic diagram of a drilling operation 10 that can include the generation of metallic swarf according to the present disclosure. For example, drilling system 10 includes a drilling rig 2 configured to form a vertical wellbore 8 and one or more lateral wellbores 12 (from the vertical wellbore 8) from a terranean surface 4 (which can also be a body of water). The wellbores 8 and 12 extend from the terranean surface 4 into one or more subterranean formations 6. During drilling operations, as shown in the circular view, a bottom hole assembly 14 that includes a drill bit 20 is operated through a casing 16 (for example, installed on the vertical wellbore 8) to form the laterals 12. During formation of the laterals 12, the drill bit 20 drills through the casing 16 with the help of a whipstock 18 to form a window 19. Metallic debris or residue, often called swarf, is generated by the drill bit 20 when it drills through the casing 16 and/or contacts the whipstock 18. This metallic swarf is returned to terranean surface 4 in a drilling mud, where it is collected and removed.

Figure 1B:
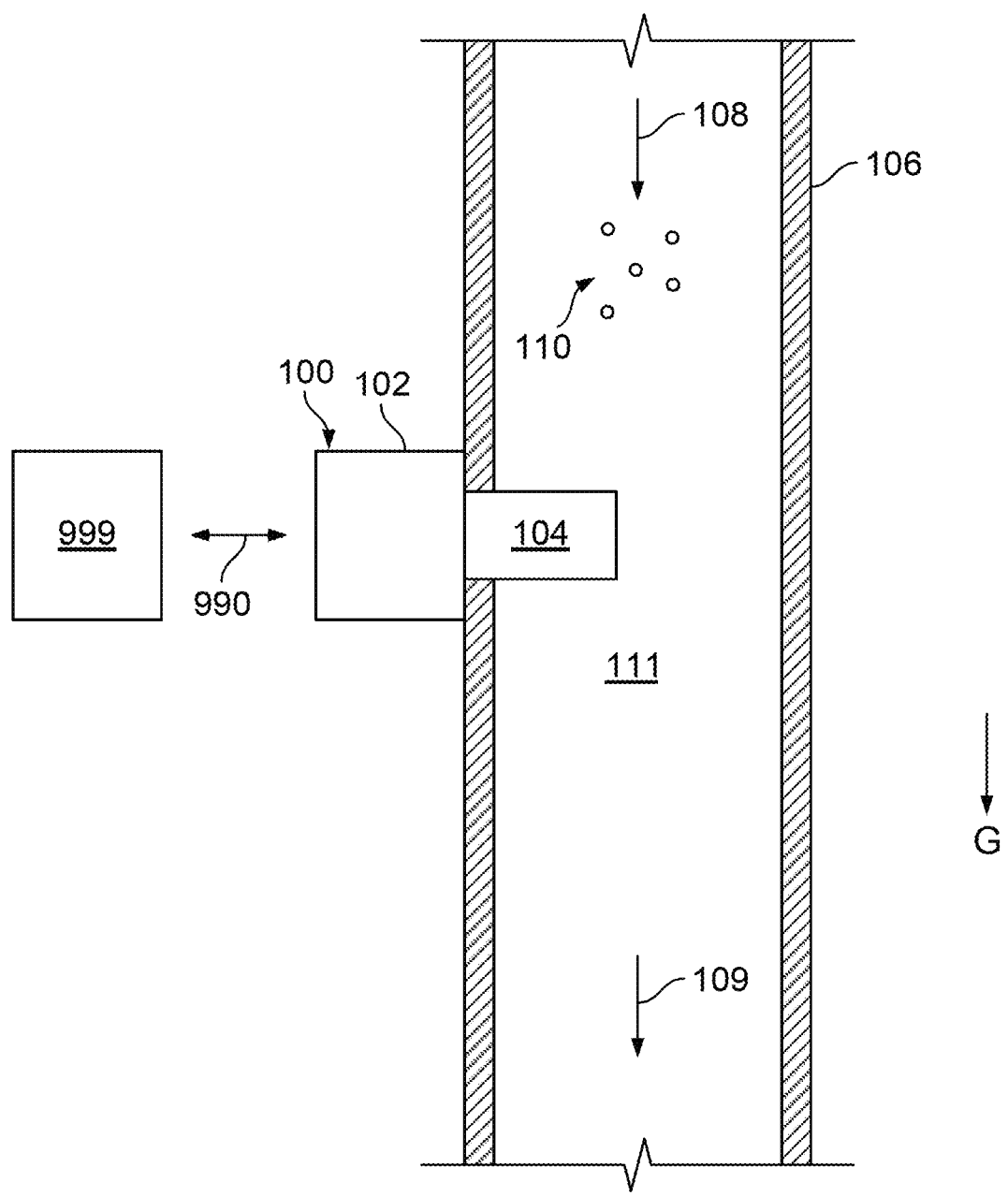
FIG. 1B is a schematic diagram of an example implementation of a metallic swarf sensor positioned in a wellbore fluid conduit according to the present disclosure.

FIG. 1B is a schematic diagram of an example implementation of a metallic swarf sensor 100 positioned in a wellbore fluid conduit according to the present disclosure. For example, when a drilling mud 108 (that includes metallic swarf 110) is circulated through a fluid conduit 106, it can pass by the metallic swarf sensor 100 (or an array of metallic swarf sensors 100), in which a magnetized portion 104 collects all or a portion of the metallic swarf 110 that flows by within fluid 108. As shown, a housing 102 couples to or external to the fluid conduit 106 (for example, a drilling mud return pipeline) so that the magnetized portion 104 extends into a flowpath 111 of the conduit 106). In some aspects, a controller 999 (for example, microprocessor, electromechanical, electrical, or otherwise) can be used to control operation (such as energizing of the magnetized portion 104) of the metallic swarf sensor 100 to collect swarf 110. Once the swarf 110 is collected (and, in some aspects, its volume sensed by the sensor 100), fluid output 109 flows away through the conduit 106. In this example, flow of the drilling mud 108 is in a direction aligned with a force of gravity (G), as shown.

Figures 2A, 2B:
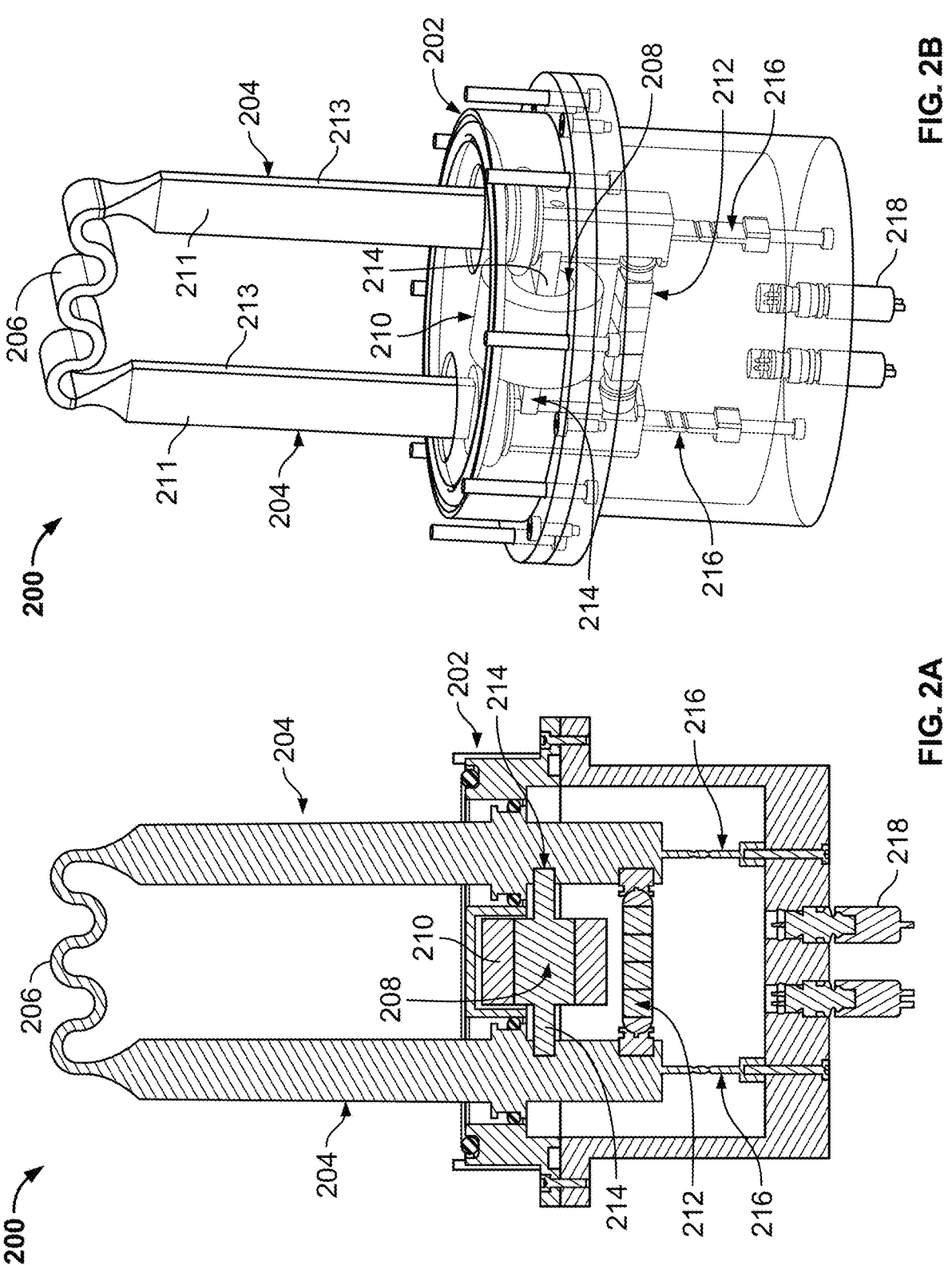
FIGS. 2A-2C are schematic diagrams of an example implementation of a metallic swarf sensor according to the present disclosure.
Figure 2C:
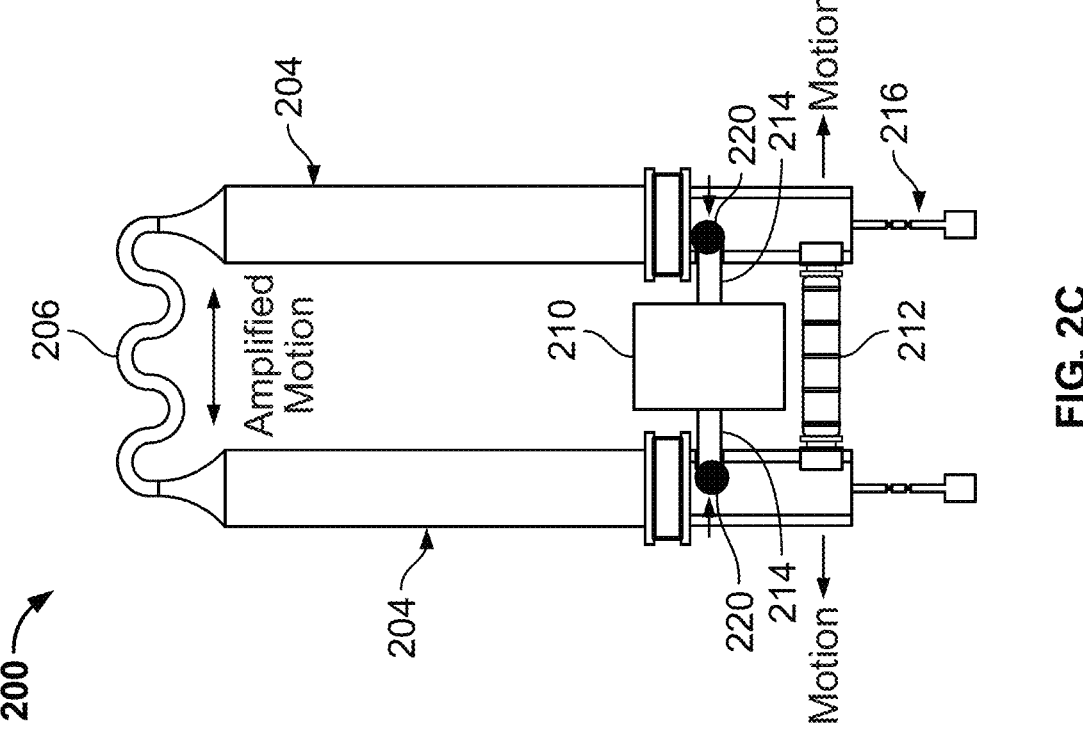

FIGS. 2A-2C are schematic diagrams of an example implementation of a metallic swarf sensor 200 according to the present disclosure. In some aspects, metallic swarf sensor 200 can be used as the metallic swarf sensor 100 shown in FIG. 1A to detect and, in addition, quantify metallic swarf in a drilling mud. For example, the metallic swarf sensor 200 can determine an amount (for example, volume or mass or both) of the metallic swarf in the drilling mud, thereby allowing a drilling operator to determine whether or not the drilling process (for example, in drilling laterals through windows with a whipstock as shown in FIG. 1A) is proceeding correctly.

FIG. 2A shows a cross-sectional view of the metallic swarf sensor 100, while FIG. 2B shows an isometric view with a housing 202 shown semi-transparent. FIG. 2C shows the movement of certain portions of the metallic swarf sensor 200 during operation. As shown in this example, metallic swarf sensor 200 includes a housing 202 from which magnetic tines 204 extend and connect by way of a magnetic flexure 206 (that, in this example, comprises a substantially sinusoidal shape). In some aspects, the housing 202 can be positioned on an exterior of a conduit with the magnetic tines 204 and magnetic flexure 206 positioned in a flowpath of drilling mud that is circulated through the conduit (as shown in FIG. 1B with metallic swarf sensor 100). Thus, the magnetic tines 204 and magnetic flexure 206 are designed to contact drilling mud and the metallic swarf in the mud. In this example, the magnetic tines 204 are blade shaped, with a flat sides 211 (2 per tine 204) and edges 213 (2 per tine 204) and a thin cross-section in one direction to minimize acoustic interaction.

The housing 202, in this example implementation, encloses a piezoelectric actuator 212 and an electromagnetic coil 210 that includes a magnetic core 208. The piezoelectric actuator stack 212 and the electromagnetic coil 210 extend between the magnetic tines 204 and, in the case of the magnetic core 208, couples to the magnetic tines 204 at core flexures 214.

Electrical feedthrough connections 218 can be electrically coupled to a source of power to energize, during an "on" operation or activation of the metallic swarf sensor 200, the electromagnetic coil 210 and piezoelectric actuator stack 212. In some aspects, a control system, such as control system 999, can provide signals 990 to turn on, or energize, the electromagnetic coil 210 through electrical feedthrough connections 218. In some aspects, the signals 990 comprise electrical signals (for example, current or voltage) that provides power through the electrical feedthrough connections 218 to, for example, the electromagnetic coil 210 and piezoelectric actuator stack 212. Thus, in some aspects, the control system 999 comprises a power source ("power source 999") for a magnetic swarf sensor according to the present disclosure.

As shown in this example, the magnetic tines 204 are connected to mounting flexures 216. The mounting flexures 216 (along with the core flexures 214) facilitate oscillatory movement of the magnetic tines 204 during operation of the metallic swarf sensor 200 (for example, when energized).

The example implementation of the metallic swarf sensor 200, therefore, comprises an electromechanical resonator with the combined piezoelectric actuator 212 and electromagnetic coil 210 that energizes to impart movement to the oscillating magnetic tines 204 that are connected through the magnetic flexure 206. An intermediate located pivot flexure is created by the electromagnetic core 208 and the piezoelectric actuator 212.

In operation, upon a flow of electricity through the electrical feedthrough connections, this electromechanical resonator is excited through the piezoelectric actuator stack 212 that imparts linear harmonic motion laterally at the lower end of the tines 204 to sweep the oscillating frequency of the magnetic tines 204 to determine a resonance frequency of the total system including swarf that is magnetically attached to the tines 204 (and flexure 206).

In this example implementation, some or all of the vibrating tine assembly—the magnetic tines 204, magnetic flexure 206, and core flexures 214—can be made of a magnetic material, such as a magnetic stainless steel metal (for example, Carpenter Alloy 430F) that can be magnetized to attract the metallic swarf. Indeed, as shown, magnetization of this structure can occur through the use of an electromagnet (the combination of the electromagnetic coil 210 and magnetic core 208), with the magnetic tines 204 connected magnetically to each other through core flexures 214 from each side of the electromagnet core 208.

The core flexures 214 form pivot points 220 (shown in FIG. 2C) that can be unsymmetrically positioned vertically between a plane in which the piezoelectric actuator stack 212 is positioned and the uncoupled ends of the tines 204 (opposite the magnetic flexure 206). The pivot point locations develop an amplification of the actuator lateral motion at the resonator tines 204, enhancing the sensitivity of the metallic swarf sensor 200 to accumulation of swarf on the surfaces of the tines 204. As shown in FIG. 2C, upon energization of the metallic swarf sensor 200, motion at the uncoupled ends of the magnetic tines 204, as well as through the magnetic flexure 206, is generated.

Figure 3:
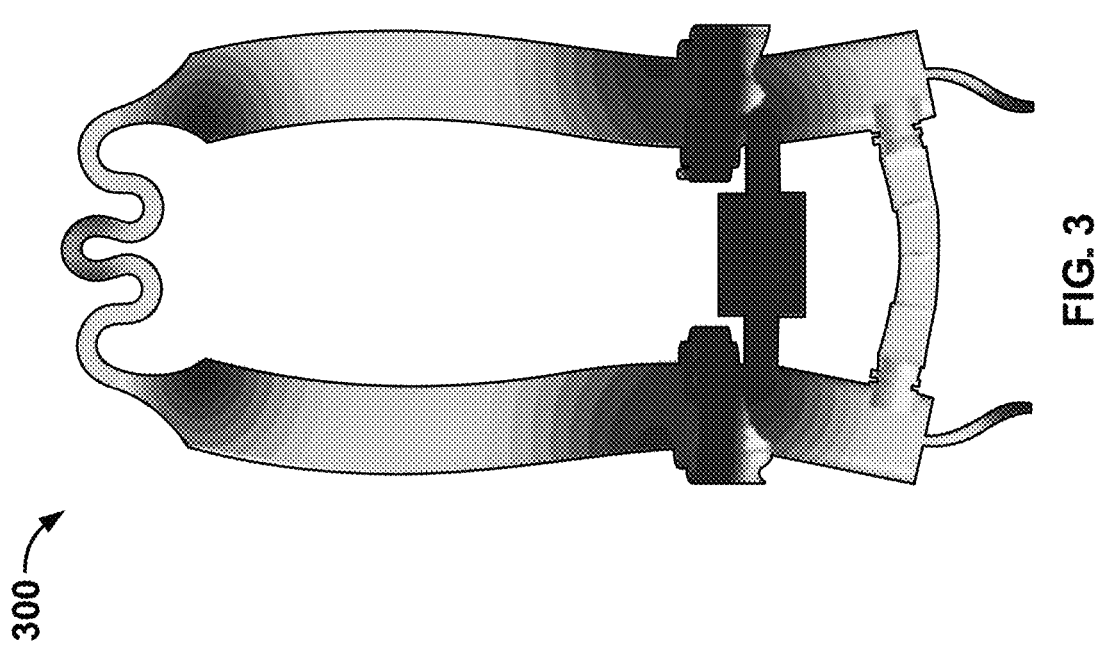
FIG. 3 is a graphic that shows a resonance frequency deformation shape of a metallic swarf sensor according to the present disclosure.

The magnetized tines 204 attract metallic (ferrous) swarf that flows with the drilling mud, such as through a surface flowline (such as conduit 106). The metallic swarf attaches to the surfaces of the vibrating tines 204. For example, FIG. 3 shown a modal deformation plot 300, which illustrates the resonance frequency deformation shape of the metallic swarf sensor 200. The modal deformation plot 300 shows a highly correlated second order degradation in resonance frequency with accumulation of added mass (the metallic swarf) on the vibrating tines 204.

Figure 4A:
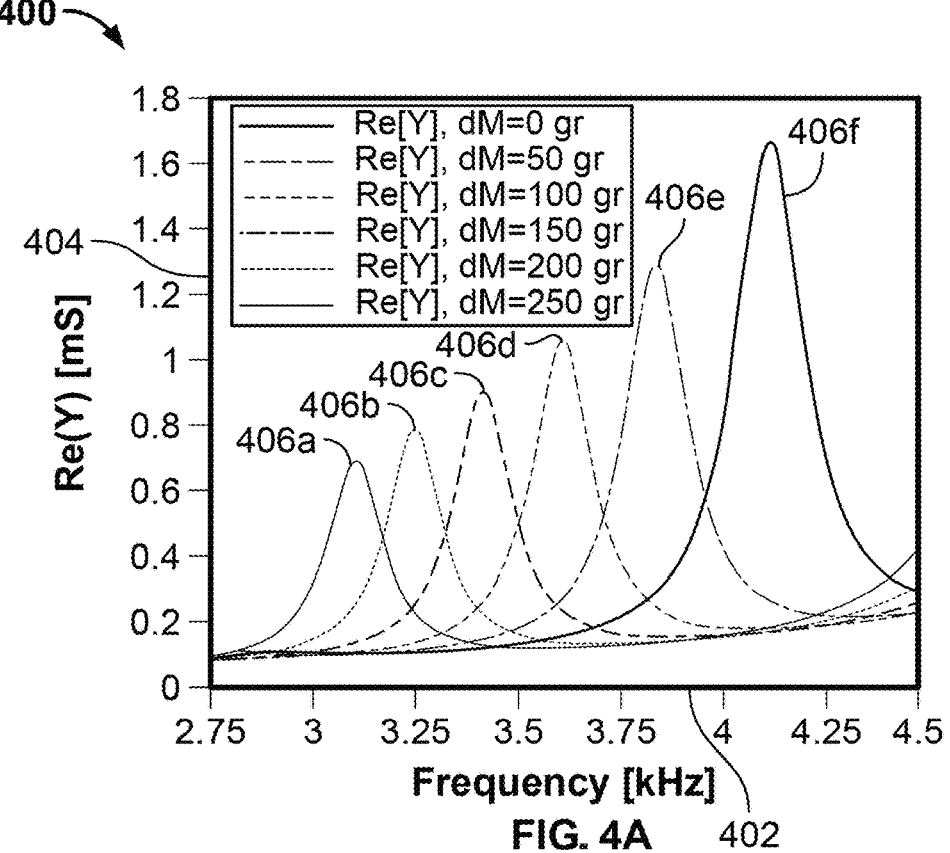
FIGS. 4A and 4B are graphs that illustrate operational characteristics of a metallic swarf sensor according to the present disclosure.
Figure 4B:
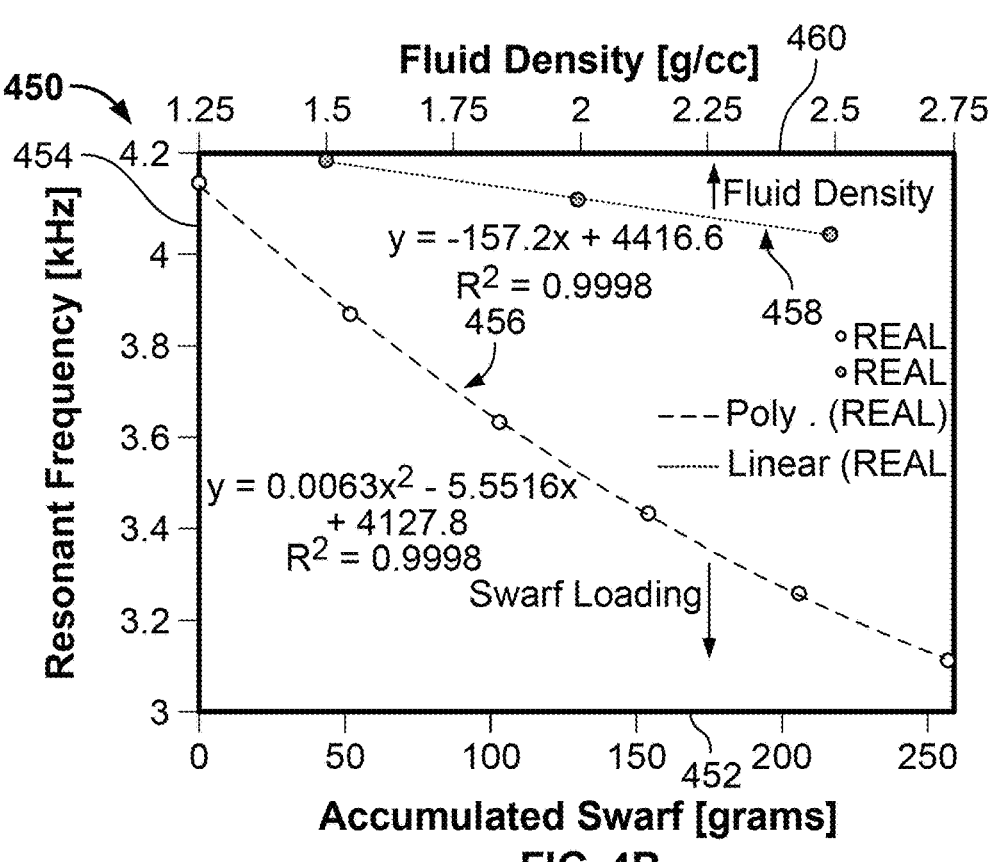

This decrease in resonance frequency of the vibrating tines 204 (due to the added mass of the attached swarf) is confirmed through a finite element analysis results shown in FIGS. 4A and 4B. FIG. 4A shows a graph 400 that illustrates electrical admittance response spectra for different magnitudes of swarf loading on the tines 204. Graph 400 includes x-axis 402 of frequency (in kHz) and y-axis 404 of electrical admittance response spectra (in mS) for curves 406a through 406f. Each curve 406a through 406f represents the electrical admittance response spectra vs. frequency for different magnitudes of mass of swarf on the tines 204 (with curve 406a representing 0 gr up to curve 406f representing 250 gr).

FIG. 4B shows a graph 450 that illustrates trends of resonance frequency with swarf loading (curve 456) and with changes in mass density of surrounding fluid media (the drilling mud, with curve 458). Graph 450 includes x-axis 452 of accumulated metallic swarf on the tines 204 (in grams), x-axis 460 of fluid (drilling mud) density (in grams per cubic centimeter), and y-axis 454 of resonance frequency (in kHz). Here, curve 456 represents the effect on resonance frequency of the tines 204 as swarf accumulates on the tines 204. Curve 458 represents the effect on resonance frequency of the tines 204 with changes to the mass density of the drilling mud (in which the metallic swarf circulates).

In some aspects, optimal operation of the metallic swarf sensor 200 occurs when the resonance frequency change is caused predominantly due to changes in swarf loading on the tines 204, and not from changes in the mass density of the drilling mud. The relative insensitivity of the metallic swarf sensor 200 to changes in fluid media mass density is illustrated curve 458 (which is relatively flat). This can be accomplished through the blade design of the magnetic tines 204 and positioning of the tines 204 in the circulating fluid (mud) with the thinner portion of the cross-section of the tines 204 (in other words, the edge of the "blade" rather than the flat) confronting a predominant direction of tine velocity in the drilling fluid stream.

In some aspects, operation of the metallic swarf sensor 200 can include a mode in which the metallic swarf sensor 200 is demagnetized in on-off cycles to allow swarf to flow out of the tines 204 (during demagnetization) rather than allowing swarf to collect on the tines 204. This on-off cycle operation can provide for, in some aspects, more accurate measurements of an amount within the drilling fluid returned from drilling operations. This on-off operation is also contrary to conventional swarf measurements using conventional ditch magnets (which collect the swarf continuously and require manual removal for intermittent measurement of accumulated swarf).

In some aspects, the metallic swarf sensor 200 can be used to measure an amount of swarf only and not collect swarf, or both measure and collect swarf. The latter operational scenario can allow the metallic swarf sensor 200 (and, in some aspects, an array of metallic swarf sensors 200) to eliminate ditch magnets (or perhaps be utilized in conjunction with ditch magnets).

The on-off example operation of the metallic swarf sensor 200 is further described with reference to FIGS. 5, 6, and 7A-7B. The off state can also include reverse degauss demagnetization, which reduces or eliminates residual magnetism from the magnetic tines 204 (as steel tines). Indeed, change in resonance frequency of the metallic swarf sensor 200 with swarf collected on the tines 204 compared to a change in resonance frequency with clean tines 204 (without accumulated swarf) is a measure of the accumulated mass of swarf attached to the tines 204. Thus, metallic swarf sensor 200 can be used in a process to monitor a whipstock sidetrack milling operation as described. This operation is graphically described in graph 500 in FIG. 5. During operation of the metallic swarf sensor 200 (or an array of metallic swarf sensors 200) within, for example, a drilling mud return line, the electromagnetic coil 210 is turned ON, represented by point (b) in graph 500. Upon reaching a predetermined resonance frequency indicative of complete swarf accumulation on the tines 204, the electromagnet coil 210 is switched OFF, represented by point (c) in graph 500. At this time, it may be desired to automatically clean all the accumulated swarf from the tines 204; however, the tines 204 remain slightly magnetized at this point and retain some coverage of swarf. To completely clean the tines 204, a reverse degauss process can be performed in which the electromagnet coil 210 applies a slight reversal in magnetic polarity indicated by point (d) in graph 500. At this point the electromagnetic coil 210 is switched OFF (point (a) in graph 500), and the tines 204 can be effectively demagnetized. Ferrous swarf can now be removed, for example, by a high frequency, high amplitude series of oscillations of the resonator tines 204. Upon automatic cleaning, the electromagnetic coil 210 is re-energized and the tines 204 are re-magnetized so that frequency sweeps can resume to determine resonance frequency changes and accordingly, to monitor swarf accumulation during the sidetrack milling operation.

Figure 6:
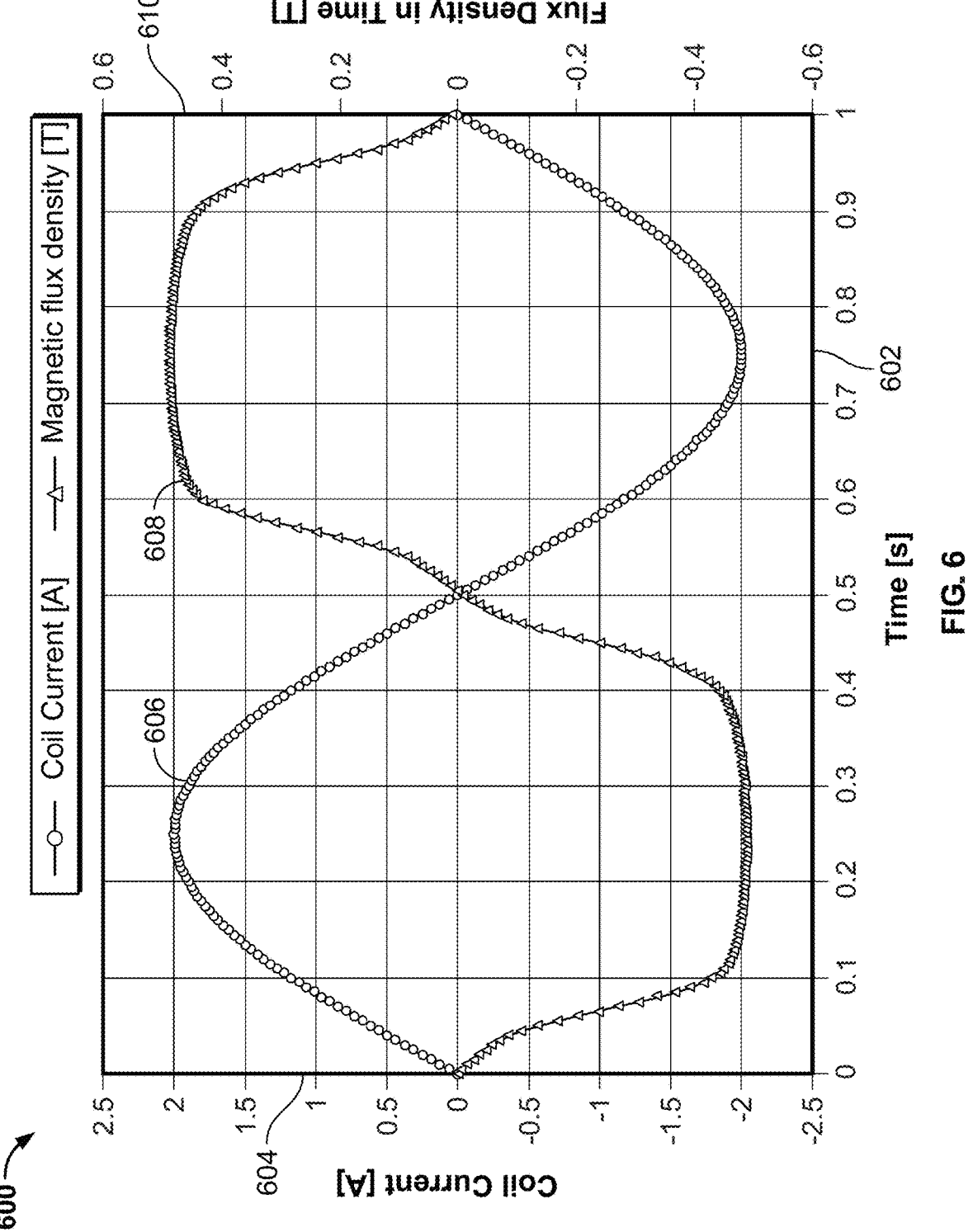
FIG. 6 is a graph that illustrates a transient ON-OFF-ON-OFF cycle for magnetization and automatic self-cleaning of a metallic swarf sensor according to the present disclosure.

The magnetic flux density in the resonator tines 204 is illustrated in FIG. 6. FIG. 6 shows a graph 600, which includes x-axis 602 of time (in seconds), y-axis 604 of coil current (in amps), and y-axis 610 of flux density in the tines 204 (in Teslas, T). Curve 606 represents the current in the electromagnetic coil 210, while curve 608 represents the magnetic flux density in the tines 204. These curves are shown for an ON-OFF-ON-OFF cycle of the metallic swarf sensor 200.

In this example, the cycle uses a coil current of 2 amps with a coil configuration having 280 turns. The resonator material is a new Carpenter 430F magnetic stainless steel alloy. Using this type of magnetic soft stainless steel and the low coil current of 2 amps can maintain the response within the linear magnetic region of the material and minimizes the hysteresis with no need for a degauss cycle. This is shown in curve 608, in which the magnetic flux density in the tines 204 returns back to zero as the coil current reaches zero. In this example, the metallic swarf sensor 200 is able to develop a high magnetic attraction field in the tines 204 and flexure 206 with a nominal flux density on the tines surface reaching 0.5 T. For a sense of attraction force, this would equate to a pull force of more than 50 pound required to separate an iron plate from the tines 204 at this instant.

Figures 7A, 7B:
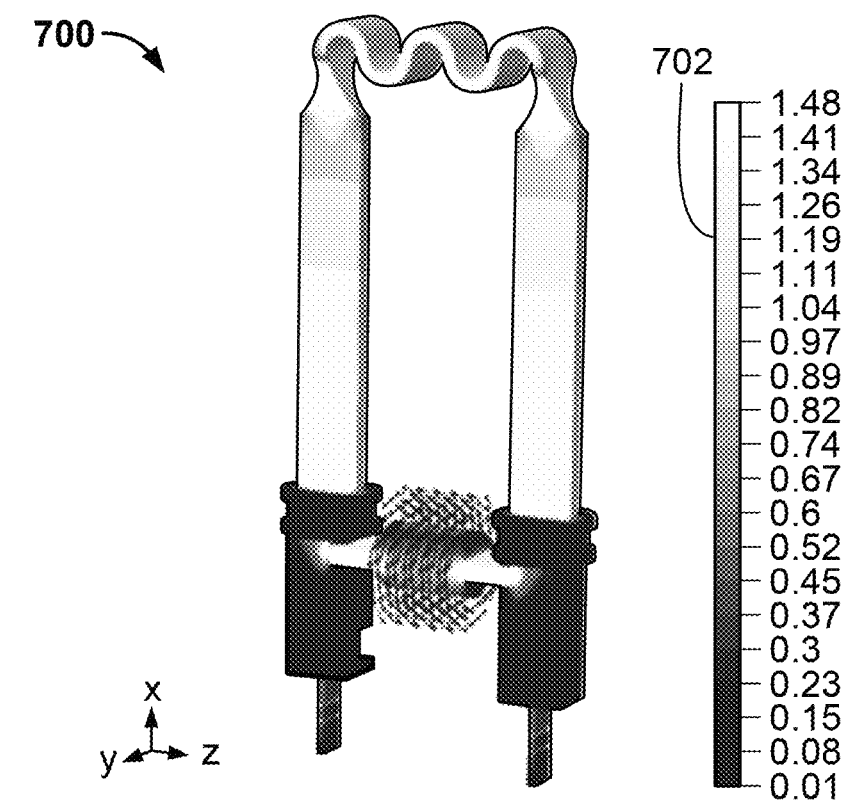
FIGS. 7A and 7B are graphs that illustrate an electromagnetic response of a metallic swarf sensor according to the present disclosure.

For the example implementation of the metallic swarf sensor 200, the magnetic flux density distribution in the resonator structure is illustrated in FIGS. 7A and 7B. FIG. 7A shows a contour plot 700 (with Tesla scale 702) of a relatively high concentration of magnetic flux throughout the entire tine and flexure structure (tines 204 and flexure 206).

The distribution of the magnetic field along the surface of the tines 204 and flexure 206 is shown in the path length plot of FIG. 7B. FIG. 7B shows graph 750, which includes x-axis 752 of arc length (in mm) and y-axis 754 of magnetic flux density norm (in Teslas). The curve 756 in graph 750 is a path plot of magnetic flux on the surface of the tines 204 (and flexure 206), starting at a tine base and following a path to a tine tip, along the magnetic flexure 206, and then down the opposite tine to its base. Curve 756 shows that the magnetic flux density in the tine assembly (tines 204 plus flexure 206) exposed to the swarf loaded stream is typically more than 0.5 T. In some aspects, the pivot flexure from the electromagnetic core 208 enables a balance between mechanical flexibility for amplification of the tine resonant motion, with a net cross section to inhibit magnetic flux saturation, and hysteresis in the magnetic cycle.

Figures 8A, 8B:
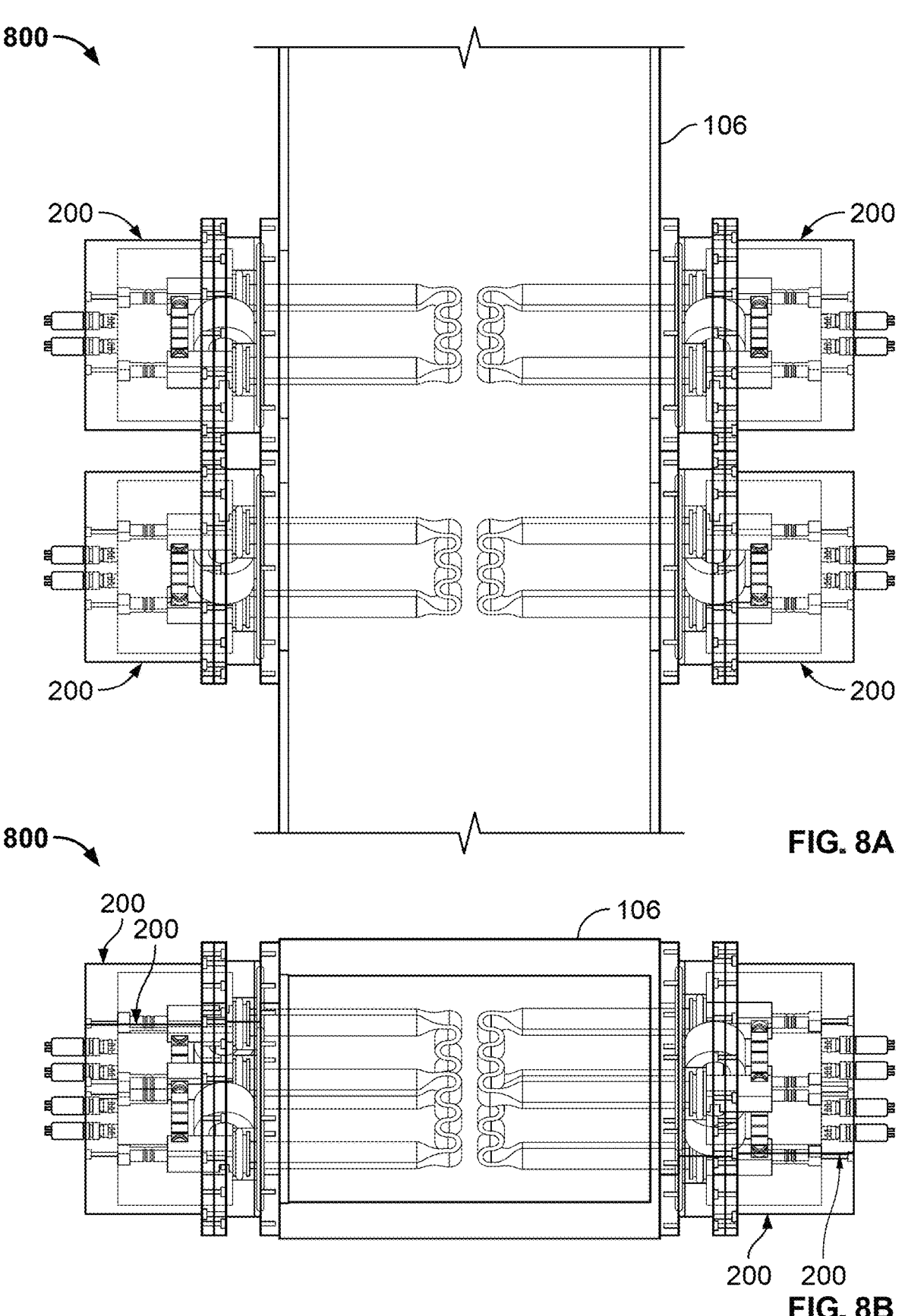
FIGS. 8A-8D are schematic diagrams of an example implementation of a metallic swarf sensor array that includes multiple metallic swarf sensors according to the present disclosure.
Figures 8C, 8D:
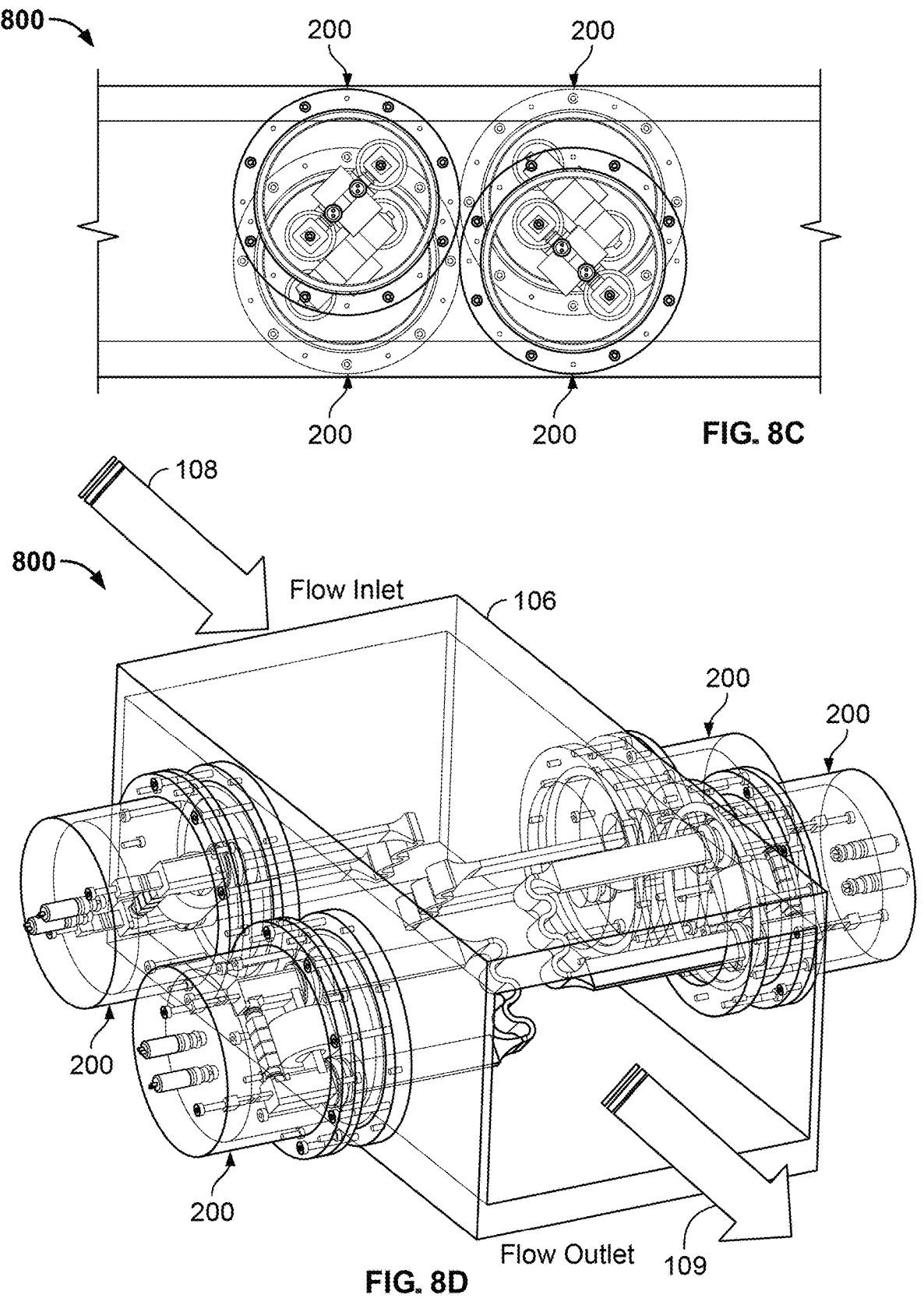

FIGS. 8A-8D are schematic diagrams of an example implementation of a metallic swarf sensor array 800 that includes multiple metallic swarf sensors 200 according to the present disclosure. As noted, in some drilling operations, it can be advantageous to install multiple metallic swarf sensors, such as metallic swarf sensor 200 or a metallic swarf sensor 900 (as described herein) or any metallic swarf sensor according to the present disclosure in a drilling mud return conduit, such as the conduit 106 shown in FIGS. 8A-8D. FIG. 8A shows the metallic swarf sensor array 800 (with an exemplary number of four metallic swarf sensors 200 or 900 positioned in a portion of the conduit 106) in a plan or top view. FIG. 8B shows the metallic swarf sensor array 800 in a "gunshot" or front view. FIG. 8C shows the metallic swarf sensor array 800 in a side view. FIG. 8D shows the metallic swarf sensor array 800 in an isometric view, with the drilling fluid 108 entering the portion of the conduit 106 in which the metallic swarf sensors 200 are mounted and leaving as fluid output 109.

As shown in this example of the metallic swarf sensor array 800, two metallic swarf sensors 200 are positioned on the conduit 106 at opposite sides. And in some aspects, conduit 106 represents a moveable section of a drilling fluid piping network that can be moved an installed in the piping network at various locations, with the array of metallic swarf sensors 200 already installed in the conduit 106. Thus, in such an example implementation, the conduit 106 (with pre-installed metallic swarf sensors 200) can be coupled (for example, threadingly or otherwise) into a drilling fluid piping network at the terranean surface 4.

As shown in this example implementation, the tines can be designed with hydrodynamic features (and the metallic swarf sensors 200 can be mounted to enhance the features) that reduce drag and minimize non-swarf debris accumulation and maintain a high accuracy of mass measurement (in other words, streamlined). Also, in some aspects, positioning of the metallic swarf sensors 200 in the conduit 106 (and blade design of the tines 204) can enable a drilling mud return flow through the magnetic tines 204 vertically to ensure gravity assists to reduce debris accumulation in the metallic swarf sensors 200. In order to create coverage of the flow cross-section for accurate measurement of swarf developed during milling, the array 800 of sensors 200 can be deployed in an arrangement with alternately angled resonator tines relative to the swarf loaded flow stream as depicted in FIG. 8D that also enables gravity assist in the automatic cleaning step of the operation (as previously described).

FIGS. 9A-9G are schematic diagrams of another example implementation of a metallic swarf sensor 900 according to the present disclosure. In some aspects, metallic swarf sensor 900 can be used as the metallic swarf sensor 100 shown in FIG. 1A to detect and, in some instances, collect metallic swarf in a drilling mud. In some aspects, the metallic swarf sensor 900 can also determine an amount (for example, volume or mass or both) of the metallic swarf in the drilling mud, thereby allowing a drilling operator to determine whether or not the drilling process (for example, in drilling laterals through windows with a whipstock as shown in FIG. 1A) is proceeding correctly.

Figure 9A:
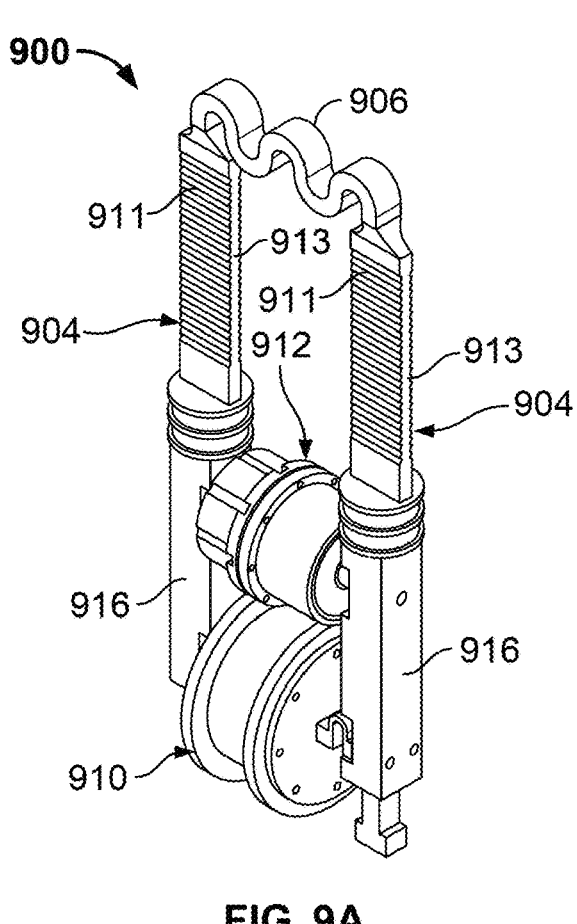
Figure 9B:
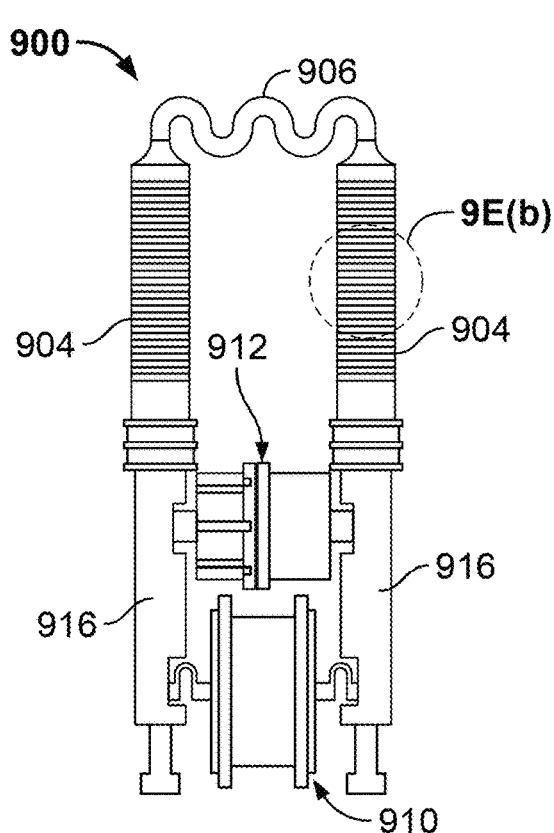
Figure 9C:
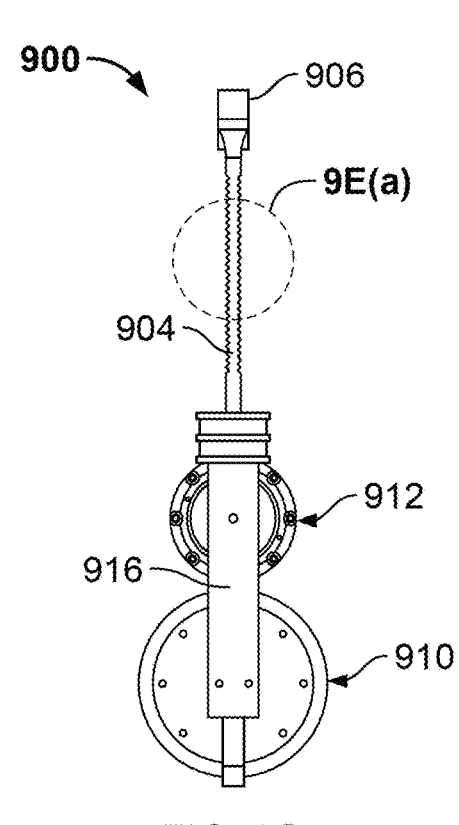
Figure 9D:
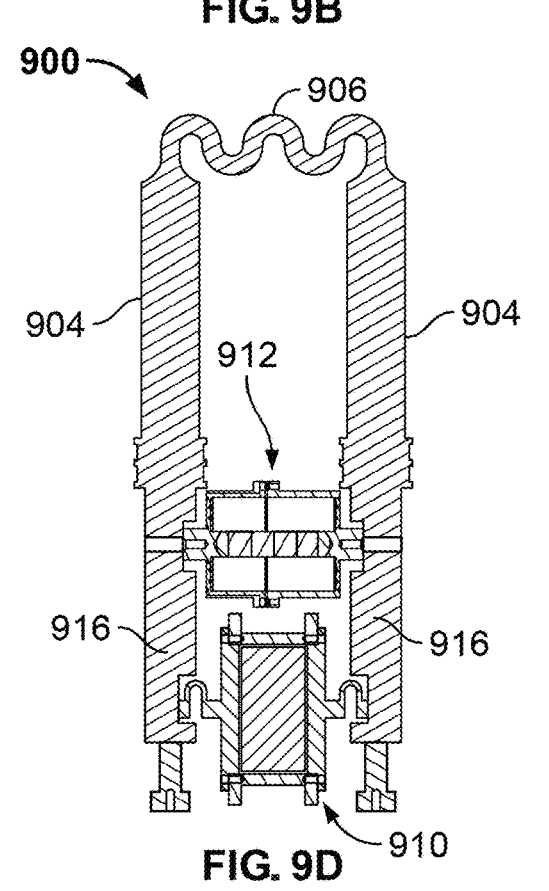

FIG. 9A shows an isometric view of the metallic swarf sensor 900. FIG. 9B shows a front view of the metallic swarf sensor 900. FIG. 9C shows a side view of the metallic swarf sensor 900. FIG. 9D shows a cross-sectional view of the metallic swarf sensor 900. FIG. 9E shows two views of a portion of a magnetic tine 904 of the metallic swarf sensor 900, with view (a) showing a side detail from FIG. 9C and view (b) showing a front detail from FIG. 9B. FIG. 9F shows a bottom view of the metallic swarf sensor 900. FIG. 9G shows a top view of the metallic swarf sensor 900.

Although not shown in this example implementation, metallic swarf sensor 900 can include a housing much like the housing 202 of the metallic swarf sensor 200. Otherwise, the metallic swarf sensor 900 includes a permanent magnet assembly 910 that spans between magnetic tines 904 replacing the electromagnetic coil from the metallic swarf sensor 200. The metallic swarf sensor 900 also includes a magnetic flexure 906 that spans the tips and connects the magnetic tines 904. In some aspects, a housing of the metallic swarf sensor 900 can be positioned on an exterior of a conduit with the magnetic tines 904 and magnetic flexure 906 positioned in a flowpath of drilling mud that is circulated through the conduit (as shown in FIG. 1B with metallic swarf sensor 100). Thus, the magnetic tines 904 and magnetic flexure 906 are designed to contact drilling mud and the metallic swarf in the mud. In this example, the magnetic tines 904 are blade shaped, with relatively flat sides 911 (2 per tine 904) and edges 913 (2 per tine 904), and a thin cross-section in one direction to minimize acoustic interaction (as explained in more detail with reference to views (a) and (b) of FIG. 9E).

Figures 10A, 10B, 10C, 10D:
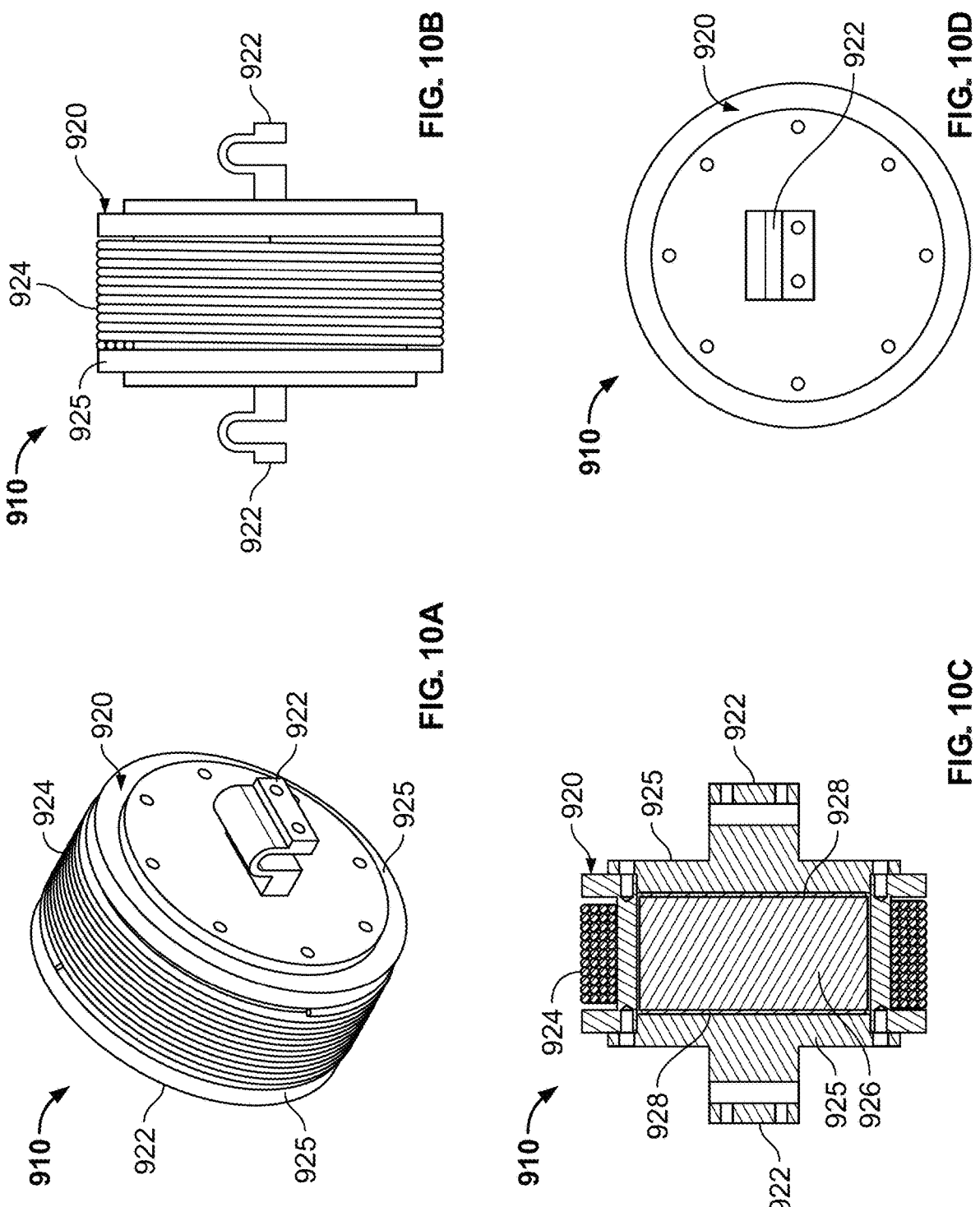
FIGS. 10A-10D are schematic diagrams of a portion of the example implementation of the metallic swarf sensor of FIGS. 9A-9G.

Turning briefly to FIGS. 10A-10D, these figures show more detail on the example implementation of the permanent magnet assembly 910 according to the present disclosure. FIG. 10A shows an isometric view of the permanent magnet assembly 910. FIG. 10B shows a front view of the permanent magnet assembly 910. FIG. 10C shows a front, cross-sectional view of the permanent magnet assembly 910. FIG. 10D shows a side view of the permanent magnet assembly 910.

In this example implementation, the permanent magnet assembly 910 includes a poling coil 924 that wraps around a permanent magnet 926. The permanent magnet 926 is enclosed by a housing 920 (around a portion of which wraps the poling coil 924. The housing 920, in this example, includes magnetic flexure panels that extend from each side of the housing 920 and couple to the magnetic tines 904 (as shown in FIG. 9A for example). Buffer pads (for example, of an elastomer) 928 are positioned between the permanent magnet 926 and the interior of housing 920. Poling coil 924 is electrically connected to electrical feedthrough connections (not shown), such as connections 218. The connections can provide an electric pulse to the poling coil 924 during a cleaning operation (for example, controlled by control system 999).

In some aspects, use of the permanent magnet assembly 910 rather than the electromagnetic coil 210 in the example implementation of metallic swarf sensor 200 can provide one or more advantages. For instance, the permanent magnet assembly 910 can provide for greater magnetic attraction of milled particles (swarf) as compared to the use of low amplitude currents in an electromagnetic coil. Furthermore, the permanent magnet assembly 910 can provide for an approximately five-times increase in a magnetic flux through the tines 904 (compared to the magnetic flux through tines 204 from the electromagnetic coil 210). Also, the permanent magnet assembly 910 can reduce or eliminate a need for active cooling to accommodate a continuous heat generation from an electromagnetic coil. An automatic cleaning cycle at the end of each swarf accumulation cycle for metallic swarf sensor 900 is accomplished using the poling coil 924 that is circumferentially surrounding the cylindrical shaped (in this example) permanent magnet 926.

In this example, the poling coil 924 is wound on a central housing (housing 920) that acts as a bobbin during coil fabrication. The housing 920 can be fabricated from a nonmagnetic material in order to prevent magnetic short-circuit of the flux to (resonator) tines 904. Structural end panels 925 attach to the ends of the housing 920 to retain the permanent magnet 926 therein. The end panels 925 can be fabricated from a high magnetic permeability material to couple the flux from the permanent magnet 926 into the resonator tines 904. To prevent cracking of the permanent magnet 926 (which can be relatively brittle) during assembly of the central housing 920 and end panels 925, the pair of elastomeric buffer pads 928 can be bonded to respective axial faces of the permanent magnet 926 and allowed to compress during assembly. Each end panel 925 can integrate the axial flexure 922 that isolates the permanent magnet 926 from forces developed during assembly of the permanent magnet assembly 910.

In some aspects, a selection of a material and geometry of permanent magnet 926 can be dictated by several considerations. These derive from the coupling of the structural design of the permanent magnet assembly 910, which can cause spurious vibrational modes to affect the overall resonance frequency characteristics of the metallic swarf sensor 900. The most sensitive design variable in this respect can be the aspect ratio of the geometry of the permanent magnet 926; that is, a ratio of the length to diameter (L/D), which can be required to be (relatively) very small in order to minimize this detrimental modal coupling. The L/D ratio optimal for proper magnetic function, in some aspects, however, can vary significantly depending upon the material selected for the permanent magnet 926.

A magnet is said to be "magnetized" when essentially all areas (called domains) of the magnet are contributing to the net magnetic field and "point" in the same direction. When only a portion of domains point in the same direction, then the other misaligned domains do not "contribute" to magnetic flux and the magnet is partially magnetized. In the event that all the domains randomly point in different directions, the magnet is demagnetized, and there is no net useable magnetic field. A magnet alloy that is susceptible to "self-demagnetization" must be magnetically long compared to the pole area for development of a net useable magnetic field. This magnetic L/D parameter can be considered in conjunction with the material magnetic properties to judge the degree of self-demagnetizing effect a magnet will encounter.

For this reason, a rare Earth NdFeB (such as the commercial grade N52) can be used as a magnet material for the metallic swarf sensor 900 due to an achievable L/D ratio as small as approximately 0.5. In comparison, another common alloy, Alnico 5, with good remanent flux density but poor coercivity, may require an L/D ratio of more than 4, leading to practically unusable resonance frequency characteristics in the metallic swarf sensor 900.

Figures 11A, 11B:
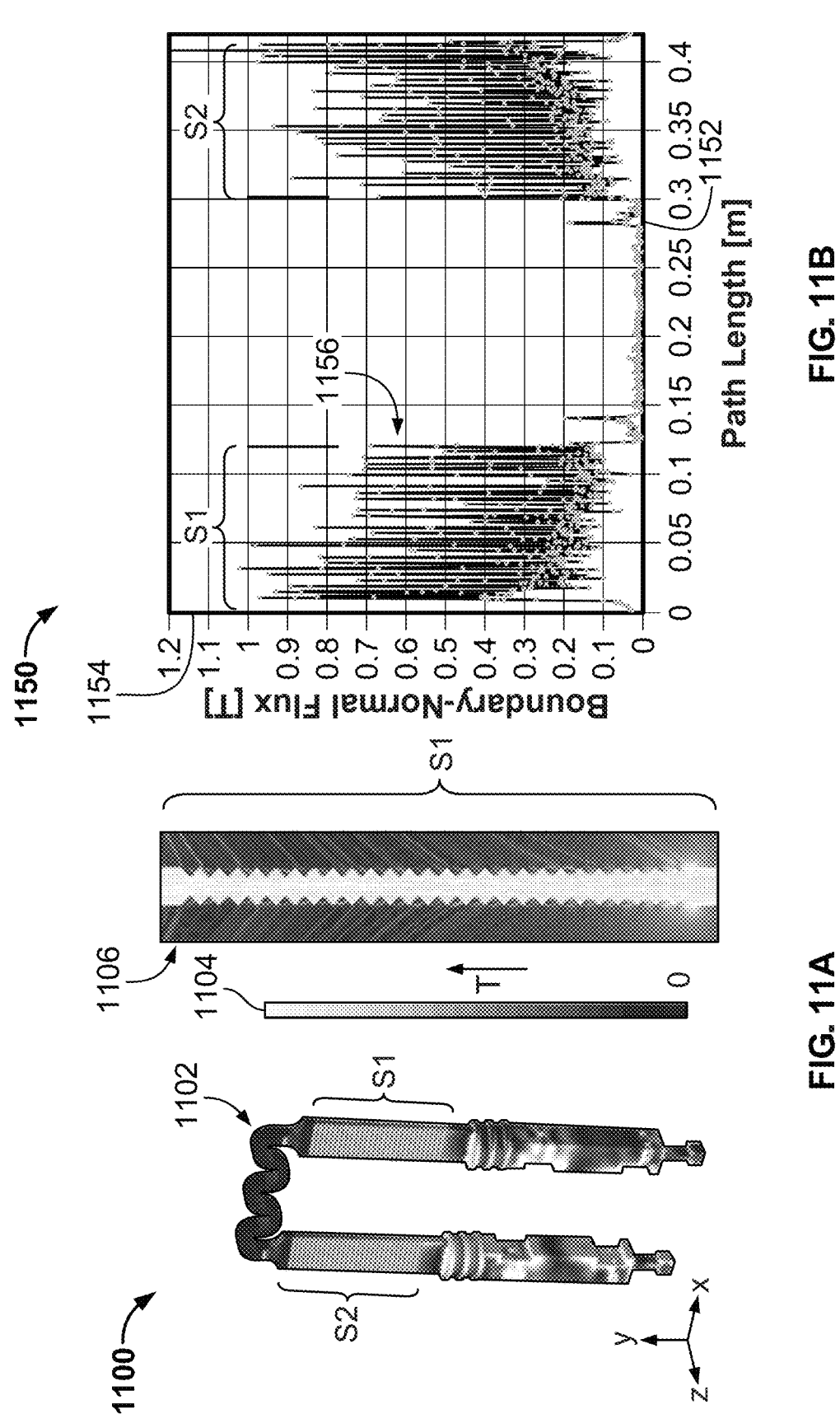
FIGS. 11A and 11B are graphs that illustrate an electromagnetic response of a metallic swarf sensor according to the present disclosure.

FIGS. 11A and 11B are graphs that illustrate an electromagnetic response of the metallic swarf sensor 900 that utilizes the permanent magnet assembly 910 and toothed structure of the magnetic tines 904. For example, FIG. 11B shows a graph 1100 that illustrates a boundary normal component of magnetic flux in the magnetic tine assembly (tines 904 and flexure 906), as well as a graph 1106 that shows a boundary normal component of magnetic flux in the magnetic tines 904. Scale 1104 shows the scale of the magnetic flux in Tesla and is limited at 0.15 T maximum to visually illustrate the zone "S" of highest attraction for metal swarf. In this example, the material of the permanent magnet 926 is NdFeB N52 grade. The inset for S1 in graph 1106 shows the confinement of magnetic flux lines between tine teeth (917) that creates the concentration zones for swarf attraction.

FIG. 11B shows a graph 1150 of boundary-normal flux vs. path length for the magnetic tine assembly (tines 904 and flexure 906). Graph 1150 includes x-axis 1152 of path length (in meters) and y-axis 1154 of magnetic flux (in Teslas). Curve 1156 represents the line plot of boundary normal flux for the edge path along one tine 904, then the flexure 906, and finally along the second tine 904. Note the concentration of boundary normal flux in the toothed zones and the relative quiescent flux leakage in the flexure and tines base in curve 1156. This can allow restriction of the accumulated swarf to only within specific tine areas that promote ease of calibration.

Returning to FIGS. 9A-9G, the metallic swarf sensor 900, in this example implementation includes a piezoelectric actuator 912 that is positioned between (and mechanically coupled to, but magnetically isolated from) the magnetic tines 904. Compared to the example implementation of the metallic swarf sensor 200, the piezoelectric actuator 912 is positioned closer to the magnetic flexure 906 as compared to the permanent magnet assembly 910 rather than further from the magnetic flexure 906 (as is the case for the piezoelectric actuator 212 compared to electromagnetic coil 210). This positioning of the piezoelectric actuator 912 can promote isolation of spurious modal coupling in the measurement spectrum for metallic swarf sensor 900 and address issues related to spurious coupled modes within the resonance frequency bandwidth that can prevent an automatic measurement of shifts in resonance frequency due to swarf accumulation on the tines 904.

Figures 14A, 14B, 14C, 14D, 14E, 14F:
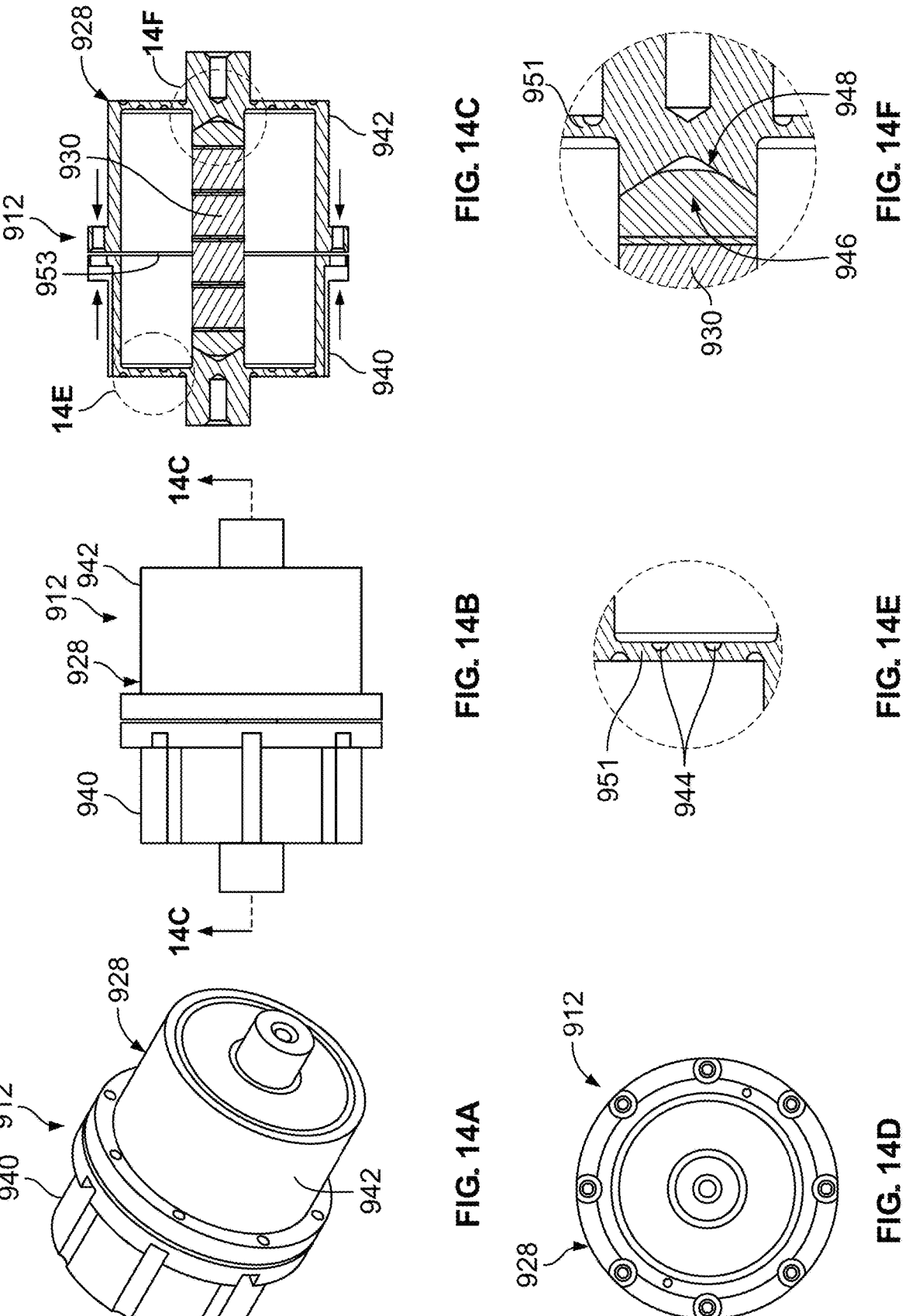
FIGS. 14A-14F are schematic diagrams of a portion of the example implementation of the metallic swarf sensor of FIGS. 9A-9G.

Turning briefly to FIGS. 14A-14F, these figures are schematic diagrams of the piezoelectric actuator 912 of the metallic swarf sensor 900. FIG. 14A shows an isometric view of the piezoelectric actuator 912. FIG. 14B shows a side view of the piezoelectric actuator 912. FIG. 14C shows a side cross-sectional view of the piezoelectric actuator 912 during a preload operation to assemble the piezoelectric actuator 912. FIG. 14D shows an end view of the piezoelectric actuator 912. FIG. 14E shows a detail of the piezoelectric actuator 912 from FIG. 14C. FIG. 14F shows another detail of the piezoelectric actuator 912 from FIG. 14C.

As shown in these figures, the example implementation of the piezoelectric actuator 912 includes a housing 920 that includes end portions 940 and 942 that, when assembled, form the housing 920. The housing 920 encloses the piezo actuator stack 930. As shown in the detail of FIG. 14E, each end panel 940 and 942 can include deflection grooves 944. As shown in the detail of FIG. 14F, each end panel 940 and 942 can include a preload pad 946 and a preload cone 948.

In some aspects, a preload is applied during assembly of the piezoelectric actuator 912 using tooling to deform the mated end panels 940 and 942 to form housing 928 by closing a flange gap 953 as illustrated in FIG. 14C (with arrows illustrating motion to close the gap 953). The deflection grooves 944 can develop elastic compliance in the piezoelectric actuator 912 and preload.

Preload on the piezoelectric actuator 912 is developed through deflection of the end panel membranes 951 of the end panels 940 and 942 during assembly. In some examples, one of the end panels 940 or 942 is pre-deformed by a total deflection needed to close the flange gap 953 using tooling that maintains the deformed membrane 951 shape during assembly onto the piezo actuator stack 930 and other end panel (940 or 942). In some aspects, to increase the membrane bending compliance of the housing end panels 940 and 942, the membrane design incorporates a series of concentric ring grooves 944 as illustrated in FIG. 14E. The ring grooves 944 can produce significant bending flexibility but limit the stress in the end panels 940 and 942 during preload.

Figure 15:
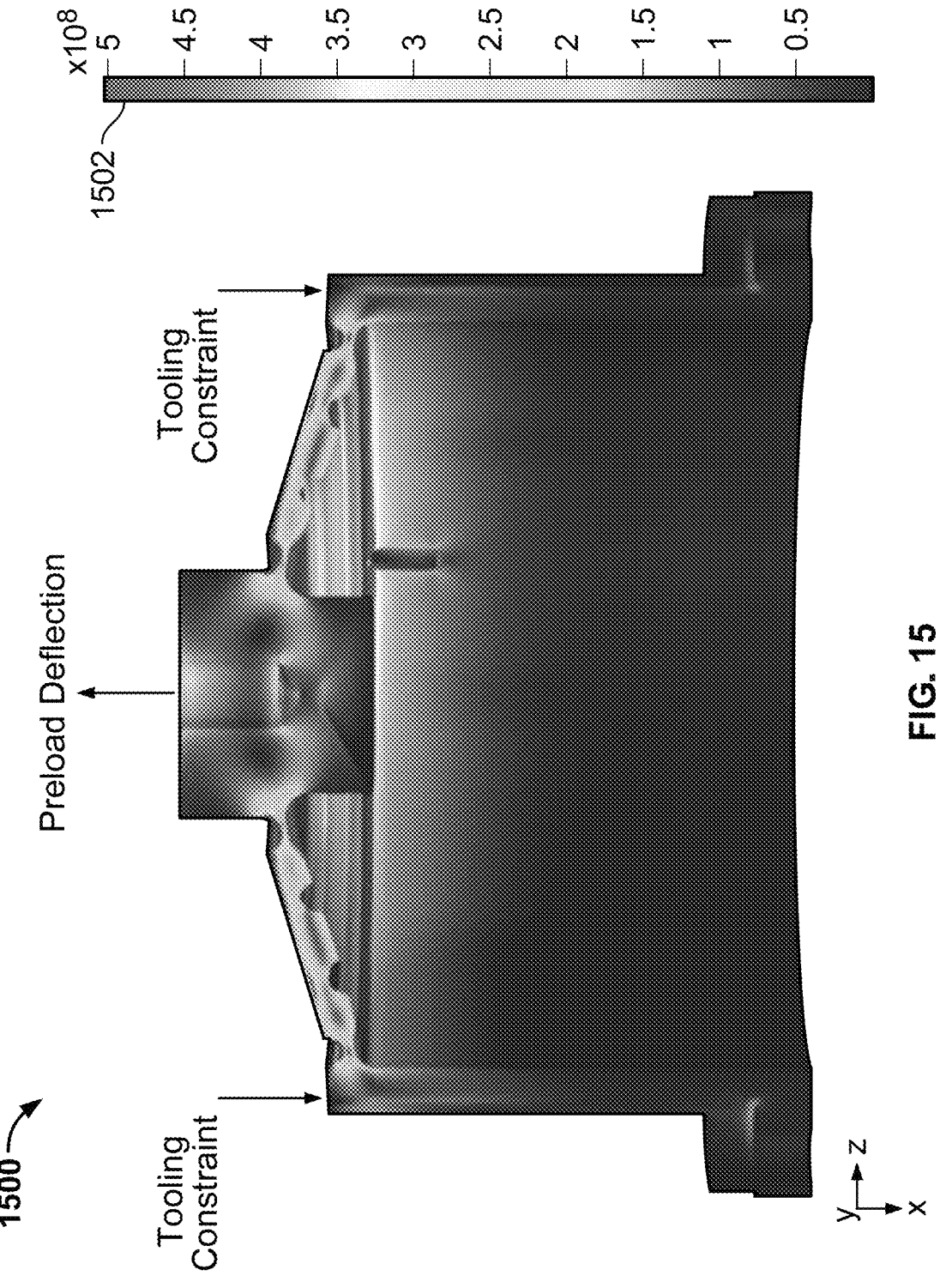
FIG. 15 is a graph that illustrates housing stress on a component of a metallic swarf sensor due to preloading deformation according to the present disclosure.

The deformed shape and associated stress distribution are shown in FIG. 15, which shows a graph 1500 with scale 1502. Graph 1500 shows (by grayscale color) the stress distribution in the piezoelectric actuator 912 during preloading assembly. After fastening the two end panels 940 and 942, the tooling is slowly dis-assembled to preload the piezoelectric actuator 912 in a controlled manner. The preloaded actuator 912 can be, at that point, part of a stand-alone actuator assembly that is inserted in the resonator tine assembly (the tines 904 coupled by the flexure 906) in combination with the permanent magnet assembly 910 and then fastened with bolts (as shown in FIG. 9A). The compliance in the end panel flexures 922 of the permanent magnet assembly 910 can prevent any additional tension or compression on the piezoelectric actuator preload that could potentially be superimposed due to fabrication tolerances buildup between the two assemblies.

Returning to FIGS. 9A-9G, as shown in this example, the magnetic tines 904 are connected to mounting flexures 916. The mounting flexures 916 facilitate oscillatory movement of the magnetic tines 904 during operation of the metallic swarf sensor 900 (for example, when energized). In this example, the magnetic tines 904 integrate a "toothed" tine resonator structure (with teeth 917). The tooth structure of the example magnetic tines 904 can provide one or more advantages over a non-toothed structure. For example, a non-toothed structure can provide insufficient confinement of the swarf mass accumulation zone on the resonator tines boundaries. The teeth 917 (and exemplary structure) can concentrate a magnetic flux within a specified zone on the boundaries to promote a more accurate mass accumulation estimation. The teeth 917, in some aspects, provide an optimum exposure area of the concentrated boundary-normal flux field by forming a type of crested right-angle pattern as shown in (a) and (b) of FIG. 9E.

The force with which the magnetic tines 904 are able to attract metallic swarf in the drilling mud flow stream can be proportional to the component of the magnetic field that "leaks out" in a direction normal to the surfaces of the magnetic tines 904. For the relatively constant cross-section tines 204 shown in the metallic swarf sensor 200, the magnetic field is securely contained in the tine assembly and develops very minimal flux leakage (for example, $B_{norm} \ll 0.01$ T) in the tine areas at 2 Amp electromagnetic coil current. In some aspects, a tine flux leakage in excess of 0.15 T can be optimal to robustly capture swarf material from the flow stream. Integration of the permanent magnet 926 can improve the flux leakage in the tines 904 (relative to tines 204 with, for example, $B_{norm} \sim 0.01$ T), which may still be insufficient for an optimal swarf accumulation. Another interrelated issue is confinement of the swarf attraction to a specific zone on each tine 904 in order to allow an accurate calibration of the resonance frequency shifts as a function of the total mass accumulation.

These two interrelated constraints cam be simultaneously satisfied by the "toothed" structure (with teeth 917) formed or integrated with each of the tines lateral surfaces, as illustrated in the detail views (a) and (b) of FIG. 9E. The resulting magnetic flux leakage component normal to the boundary surfaces is shown in the contour plot of FIG. 11A. Also, the line plot of graph 1150 shows the magnitude of boundary normal magnetic component for an outer edge path along the first tine 904 near the positive polarity face of the permanent magnet 926, then the flexure 906, and finally along the second tine 904 near the negative polarity face of the permanent magnet 926. The line plot (curve 1156) graphically illustrates the effects of the toothed geometry in creating specific zones of high flux leakage while retaining relatively quiescent flux leakage magnitudes everywhere outside these specific zones. The flux leakage remains generally between $0.15 \text{ T} < B_{norm} < 0.4$ T in the tines zone of concentrated magnetization, which is significantly enhanced relative to the metallic swarf sensor 200.

In some aspects, the integration of the "toothed" structure of the tines 904 (in other words, the periodic tooth pattern in each tine) can reduce a resonance frequency of the metallic swarf sensor 900 and improves the sensitivity of the metallic swarf sensor 900 to swarf mass accumulation. The resonance frequency reduces to a range between 1.1-1.9 kHz, compared to 3-4 kHz with metallic swarf sensor 200. The resonance frequency sensitivity to swarf mass accumulation can be approximately 40% at 4.5 g/cm² (500 gram total) for metallic swarf sensor 900, compared to about 30% in metallic swarf sensor 200.

A typical resonance frequency deformation is illustrated in FIG. 12. FIG. 12 shows graph 1200 and scale 1204, which illustrates a greyscale color scale of resonance frequency deformation in the magnetic tine assembly (tines 904 and flexure 906).

In some aspects, for example, the modified position of the piezoelectric actuator assembly 912 located intermediately between the tines 904 and the permanent magnet assembly 910, can increase the sensitivity of the metallic swarf sensor 900 while isolating the dynamics of the permanent magnet assembly 910 to prevent modal coupling contamination in the measurement spectra. The resonance mode is then tailored to achieve a more classical "tuning fork" type mode shape as illustrated in graph 1200, where the dynamics of the permanent magnet assembly 910 and the piezoelectric actuator assembly 912 are relatively quiescent compared to the tines dynamic response. For example, FIG. 13A shows sample electrical admittance spectra for different swarf mass loading in graph 1300. Graph 1300 includes x-axis 1302 of frequency (in kHz) and y-axis 1304 of electrical admittance response spectra (in mS) for curves 1306a through 1306f. Each curve 1306a through 1306f represents the electrical admittance response spectra vs. frequency for different magnitudes of mass of swarf on the tines 904 (with curve 1306a representing 0 gr up to curve 1306f representing 500 gr).

FIG. 13B shows a graph of sensitivity of the sensor resonance frequency with changes in swarf mass loading (on tines 904). FIG. 13B shows a graph 1350 that illustrates trends of resonance frequency with swarf loading (curve 1358) and with changes in mass density of surrounding fluid media (the drilling mud, with curve 1360). Graph 1350 includes x-axis 1352 of accumulated metallic swarf on the tines 904 (in grams), x-axis 1356 of fluid (drilling mud) density (in grams per cubic centimeter), and y-axis 1354 of resonance frequency (in kHz). Here, curve 1358 represents the effect on resonance frequency of the tines 904 as swarf accumulates on the tines 904. Curve 1360 represents the effect on resonance frequency of the tines 904 with changes to the mass density of the drilling mud (in which the metallic swarf circulates).

As shown, the curve 1358 is monotonic over the mass accumulation range analyzed and is seen to follow a 3rd order polynomial dependence with mass loading. In some aspects, a requirement placed on the metallic swarf sensor 900 is that the sensor resonance frequency change must be caused predominantly due to changes in swarf loading on the tines 904, and not from changes in mass density of the surrounding drilling mud stream. The relative insensitivity of the metallic swarf sensor 900 to changes in fluid media mass density is illustrated in the curves 1358 and 1360. As discussed previously, the resonance frequency sensitivity to swarf mass accumulation is approximately 40% for 500 gram tines loading. In comparison, the resonance frequency sensitivity to the surrounding fluid media is approximately ±1.6% for fluid density in the range of 2.0±1.0 g/cc. As a reference, certain formations may be drilled with a density as low as 1.0 g/cc, but other high pressure formations may require a fluid with density approaching 2.4 g/cc.

In some aspects, operation of the metallic swarf sensor 900 can include a mode in which the metallic swarf sensor 900 is demagnetized to represent an OFF cycle that interrupts an otherwise constant ON cycle from the sensor 900. In the OFF cycle, swarf is allowed to flow out of the tines 904 (during demagnetization) rather than allowing swarf to collect on the tines 904. This OFF cycle operation can provide for, in some aspects, cleaning of the tines for more accurate measurements of an amount within the drilling fluid returned from drilling operations. This on-off operation is also contrary to conventional swarf measurements using conventional ditch magnets (which collect the swarf continuously and require manual cleaning to intermittently weigh accumulated swarf).

In some aspects, the metallic swarf sensor 900 can be used to measure an amount of swarf only and not collect swarf, or both measure and collect swarf. The latter operational scenario can allow the metallic swarf sensor 900 (and, in some aspects, an array of metallic swarf sensors 900) to eliminate ditch magnets (or perhaps be utilized in conjunction with ditch magnets). Since a surface area of the magnetic tines 904 (for example, with a tine length of about 120 mm) in an array of metallic swarf sensors 900 is comparable to that of a conventional ditch magnet device, collection of swarf for removal from the drilling mud is contemplated by the present disclosure.

The on-off example operation of the metallic swarf sensor 900 is further described with reference to FIG. 5. As with the metallic swarf sensor 200, the off state of metallic swarf sensor 900 can also include reverse degauss demagnetization, which reduces or eliminates residual magnetism from the magnetic tines 904 (as steel tines). Indeed, change in resonance frequency of the metallic swarf sensor 900 with swarf collected on the tines 904 compared to a change in resonance frequency with clean tines 904 (without accumulated swarf) is a measure of the accumulated mass of swarf attached to the tines 904. Thus, metallic swarf sensor 900 can be used in a process to monitor a whipstock sidetrack milling operation as described.

Figure 5:
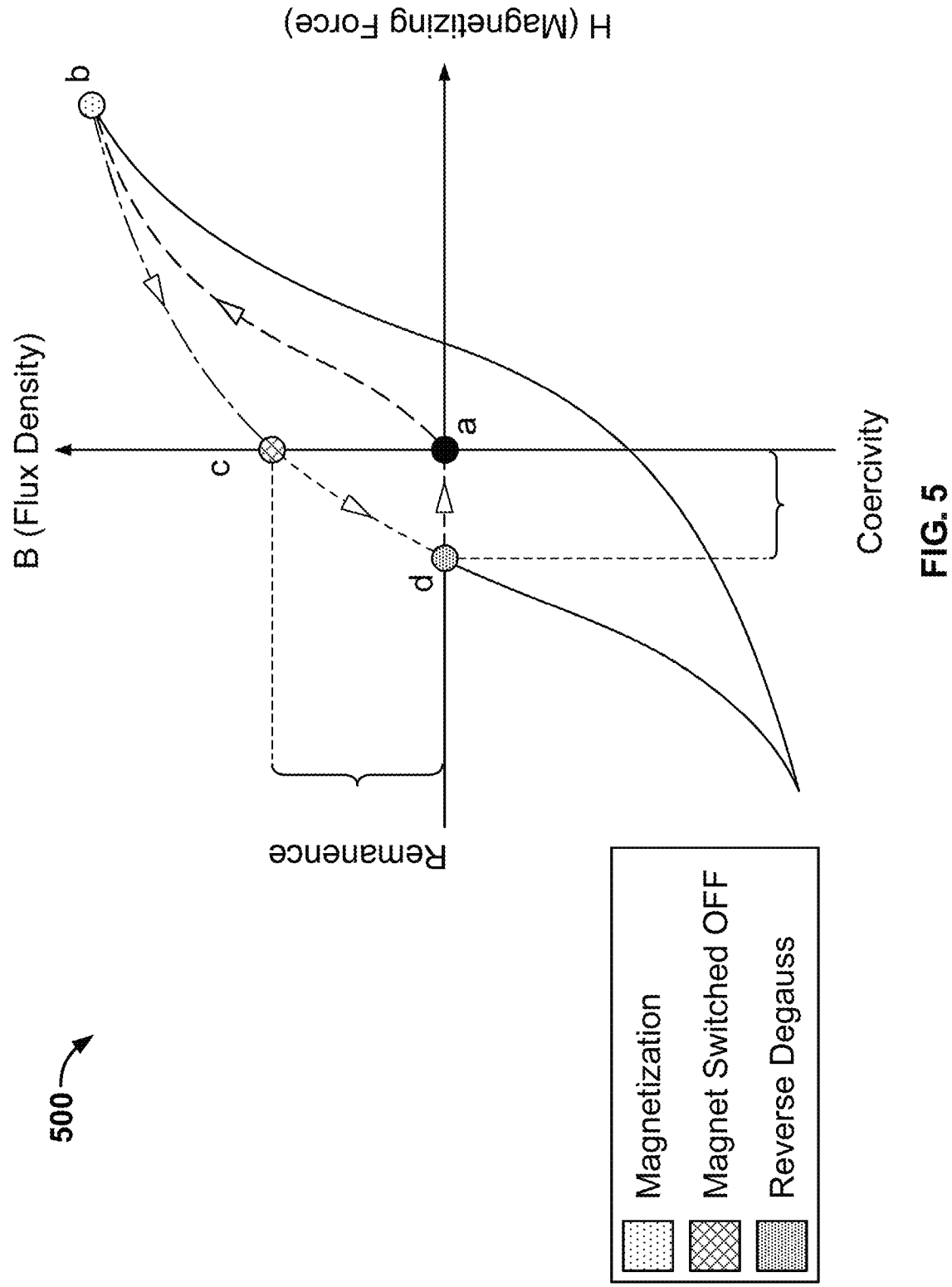
FIG. 5 is a graph that illustrates a reverse degauss demagnetization effect on a metallic swarf sensor according to the present disclosure.

This operation for metallic swarf sensor 900 is also graphically described in graph 500 in FIG. 5. However, for metallic swarf sensor 900 (unlike metallic swarf sensor 200), the switching of the magnetic field for the cleaning operation of metallic swarf sensor 900 is initiated by a current pulse applied to the poling coil 924 in sufficient magnitude to overcome an intrinsic coercivity ($H_{ci}$) for the specific permanent magnet material selected, which in effect switches the magnetic field OFF. The current magnitude (i) in the poling coil 924 necessary to depole the permanent magnet 926 can be calculated from the relation:

$$i = \left[\frac{L_{PM}}{N_{turns}}\right] H_{ci}. \qquad \text{Eq. 1}$$

In Eq. 1, $L_{PM}$ is the axial dimension of the permanent magnet 926, i is current magnitude in the poling coil 924, $H_{ci}$ is the intrinsic coercivity, and $N_{turns}$ is the total number of turns in the coil 924. This state is similar to the condition at point (d) in graph 500. A degree of residual flux density will remain in the magnetic tine material even after depoling of the permanent magnet 926, thereby requiring a degauss overcurrent to be applied in order to place the tines 904 in a quiescent magnetic state during the high amplitude tines vibration cleaning operation (in other words, the OFF state). Upon completion of the tine cleaning procedure, the current in the poling coil 924 is reversed in polarity to place the permanent magnet 926 at a state similar to point (b) in graph 500. Upon removal of the coil current from poling coil 924, the permanent magnet field switches to ON at the intrinsic remanent flux density ($B_r$), similar to point (c) in graph 500, from which the measurement process continues.

Figure 16:
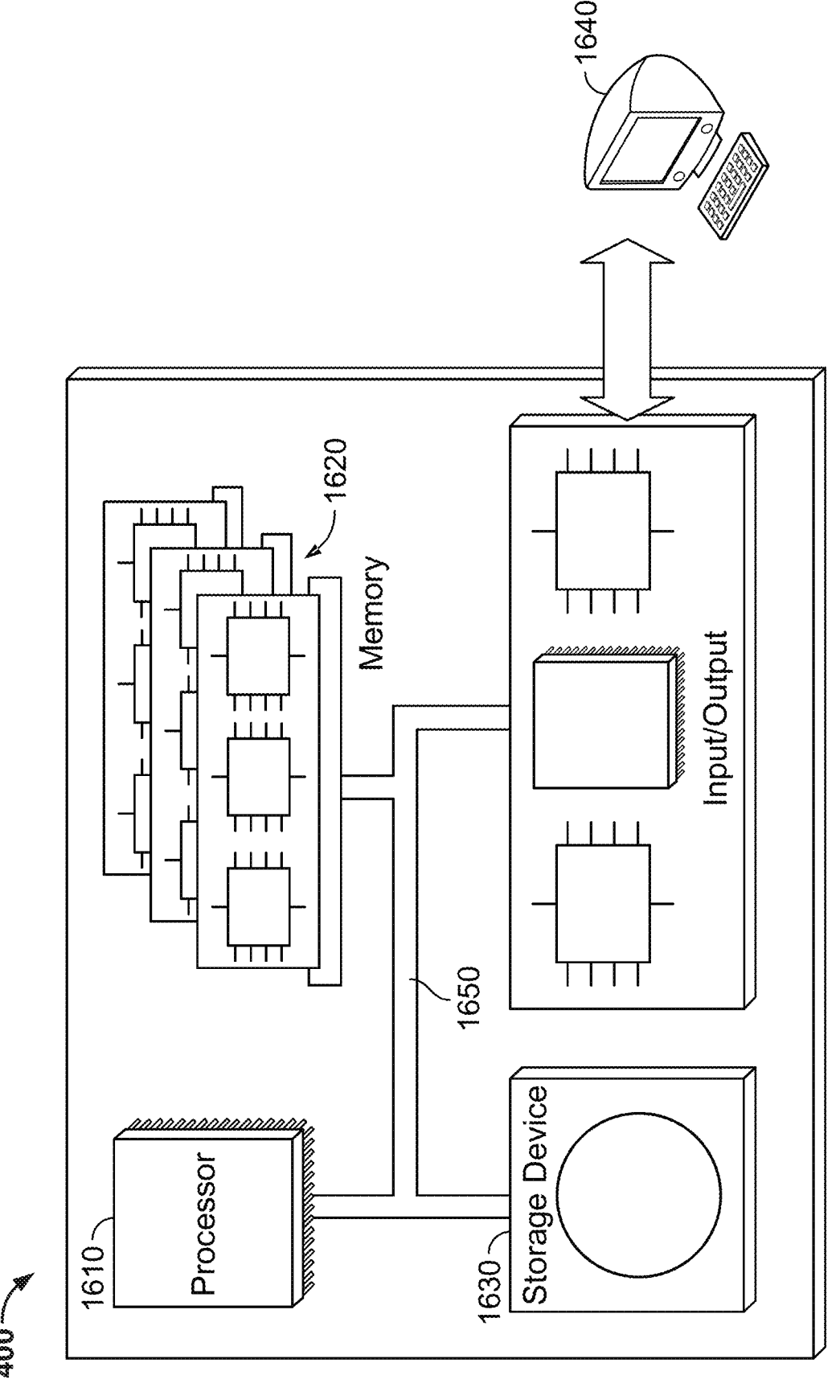
FIG. 16 shows a schematic drawing of a control system according to the present disclosure.

FIG. 16 shows a schematic drawing of a control system 1600 that can be used to control a metallic swarf sensor, or metallic swarf sensor array, according to the present disclosure and/or any processes described in the present disclosure. In some aspects, control system (or controller) 1600 can be used as all or part of control system 999. Some or all of the example control system 1600 can be implemented as cloud-based system and/or service, alone or in combination with other portions of the example control system 1600. The controller 1600 is intended to include various forms of digital computers, such as printed circuit boards (PCB), processors, digital circuitry, or otherwise. Additionally, the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 1600 includes a processor 1610, a memory 1620, a storage device 1630, and an input/output device 1640. Each of the components 1610, 1620, 1630, and 1640 are interconnected using a system bus 1650. The processor 1610 is capable of processing instructions for execution within the controller 1600. The processor may be designed using any of a number of architectures. For example, the processor 1610 may be a CISC (Complex Instruction Set Computers) processor, a RISC (Reduced Instruction Set Computer) processor, or a MISC (Minimal Instruction Set Computer) processor.

In one implementation, the processor 1610 is a single-threaded processor. In another implementation, the processor 1610 is a multi-threaded processor. The processor 1610 is capable of processing instructions stored in the memory 1620 or on the storage device 1630 to display graphical information for a user interface on the input/output device 1640.

The memory 1620 stores information within the control system 1600. In one implementation, the memory 1620 is a computer-readable medium. In one implementation, the memory 1620 is a volatile memory unit. In another implementation, the memory 1620 is a non-volatile memory unit.

The storage device 1630 is capable of providing mass storage for the controller 1600. In one implementation, the storage device 1630 is a computer-readable medium. In various different implementations, the storage device 1630 may be a floppy disk device, a hard disk device, an optical disk device, a tape device, flash memory, a solid state device (SSD), or a combination thereof.

The input/output device 1640 provides input/output operations for the controller 1600. In one implementation, the input/output device 1640 includes a keyboard and/or pointing device. In another implementation, the input/output device 1640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) or LED (light-emitting diode) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A metallic swarf sensor, comprising:
a housing configured to couple to a fluid conduit that comprises a flowpath for a circulation of a wellbore fluid that comprises metallic swarf;
a magnetic tine assembly that comprises a pair of magnetic tines that extend from the housing and connect through a magnetic flexure;
a magnetic assembly at least partially enclosed within the housing and coupled to the magnetic tine assembly, the magnetic assembly configured to magnetize the magnetic tine assembly; and
a piezoelectric actuator at least partially enclosed within the housing and coupled to the magnetic tine assembly, the piezoelectric actuator configured to resonate the magnetic tine assembly at a variable resonance frequency.

2. The metallic swarf sensor of claim 1, wherein the piezoelectric actuator is coupled to the magnetic tine assembly at a first pivot point coupled to a first magnetic tine of the pair of magnetic tines and at a second pivot point coupled to a second magnetic tine of the pair of magnetic tines.

3. The metallic swarf sensor of claim 1, wherein the magnetic assembly comprises:
a magnetic core; and
an electromagnetic coil wrapped around the magnetic core and electrically coupled to a power source through one or more electrical feedthrough connections.

4. The metallic swarf sensor of claim 3, comprising a controller electrically coupled to the electromagnetic coil and configured to perform operations comprising:
applying a current from the power source to the electromagnetic coil to magnetize the magnetic tine assembly to magnetically attract the metallic swarf to the magnetic tine assembly from the wellbore fluid;
decoupling the current from the power source to the electromagnetic coil to demagnetize the magnetic tine assembly to cease to magnetically attract the metallic swarf to the magnetic tine assembly from the wellbore fluid; and operating the electromagnetic coil to perform a reverse degauss process to clean the metallic swarf from the magnetic tine assembly.

5. The metallic swarf sensor of claim 4, wherein the current is a first current at a first magnetic polarity, and the operation of operating the electromagnetic coil to perform the reverse degauss process to clean the metallic swarf from the magnetic tine assembly comprises:
applying a second current at a second magnetic polarity that is reverse from the first magnetic polarity from the power source to the electromagnetic coil to demagnetize the magnetic tine assembly to repel the metallic swarf attached to the magnetic tine assembly.

6. The metallic swarf sensor of claim 1, wherein the magnetic assembly comprises:
a permanent magnet; and
a poling coil wrapped around the permanent magnet and electrically coupled to a power source through one or more electrical feedthrough connections.

7. The metallic swarf sensor of claim 6, comprising a controller electrically coupled to the poling coil and configured to perform operations comprising:
applying a current from the power source to the poling coil to depole the permanent magnet and switch a magnetic field generated by the permanent magnet; and
based on the switched magnetic field, demagnetizing the magnetic tine assembly to magnetically repel the metallic swarf attached to the magnetic tine assembly.

8. The metallic swarf sensor of claim 7, wherein the operation of applying the current comprises applying a current of sufficient magnitude to overcome an intrinsic coercivity of the permanent magnet.

9. The metallic swarf sensor of claim 8, wherein the current of sufficient magnitude is determined by:

$$i = \left[\frac{L_{PM}}{N_{turns}}\right] H_{ci},$$

where $L_{PM}$ is an axial dimension of the permanent magnet, i is the current magnitude in the poling coil, $H_{ci}$ is the intrinsic coercivity, and $N_{turns}$ is a total number of turns of the poling coil.

10. The metallic swarf sensor of claim 1, wherein each of the pair of magnetic tines comprises a blade, and the magnetic flexure comprises a sinusoidal shape.

11. The metallic swarf sensor of claim 10, wherein the blade comprises a plurality of teeth.

12. The metallic swarf sensor of claim 1, wherein the magnetic tine assembly comprises a magnetic stainless steel alloy.

13. A method for managing metallic swarf in a drilling fluid, comprising:
circulating a drilling fluid through a flowpath of a fluid conduit that comprises at least one metallic swarf sensor coupled to the fluid conduit, the drilling fluid comprising metallic swarf;
energizing a magnetic assembly at least partially enclosed within a housing of the metallic swarf sensor that is coupled to an exterior of the fluid conduit;
based on energizing the magnetic assembly, magnetizing a magnetic tine assembly of the metallic swarf sensor that extends into the flowpath from the housing, the magnetic tine assembly comprising a pair of magnetic tines that extend from the housing and connect through a magnetic flexure;

23
24 resonating, at a variable resonance frequency, the magnetic tine assembly with a piezoelectric actuator at least partially enclosed within the housing; and magnetically attracting at least a portion of the metallic swarf in the drilling fluid to the magnetized magnetic tine assembly.

14. The method of claim 13, comprising resonating the magnetic tine assembly with the piezoelectric actuator through a first pivot point coupled to a first magnetic tine of the pair of magnetic tines and through a second pivot point coupled to a second magnetic tine of the pair of magnetic tines.

15. The method of claim 13, wherein energizing the magnetic assembly comprises providing a current from a power source to an electromagnetic coil wrapped around a magnetic core through one or more electrical feedthrough connections.

16. The method of claim 15, comprising:

magnetizing the magnetic tine assembly by providing the current from the power source to the electromagnetic coil;

magnetically attracting the metallic swarf from the drilling fluid to the magnetic tine assembly;

decoupling the current from the power source to the electromagnetic coil to demagnetize the magnetic tine assembly to cease to magnetically attract the metallic swarf to the magnetic tine assembly from the wellbore fluid; and operating the electromagnetic coil to perform a reverse degauss process to clean the metallic swarf from the magnetic tine assembly.

17. The method of claim 16, wherein the current is a first current at a first magnetic polarity, and operating the electromagnetic coil to perform the reverse degauss process to clean the metallic swarf from the magnetic tine assembly comprises:

providing a second current at a second magnetic polarity that is reverse from the first magnetic polarity from the power source to the electromagnetic coil to demagnetize the magnetic tine assembly to repel the metallic swarf attached to the magnetic tine assembly.

18. The method of claim 13, wherein energizing the magnetic assembly comprises generating a magnetic field with a permanent magnet around which is wrapped a poling coil that is electrically coupled to a power source through one or more electrical feedthrough connections.

19. The method of claim 18, comprising:

providing a current from the power source to the poling coil to depole the permanent magnet and switch a magnetic field generated by the permanent magnet; and based on the switched magnetic field, demagnetizing the magnetic tine assembly to magnetically repel the metallic swarf attached to the magnetic tine assembly.

20. The method of claim 19, wherein applying the current comprises applying a current of sufficient magnitude to overcome an intrinsic coercivity of the permanent magnet.

21. The method of claim 20, wherein the current of sufficient magnitude is determined by:

$$i = \left[\frac{L_{PM}}{N_{turns}}\right] H_{ci},$$

where $L_{PM}$ is an axial dimension of the permanent magnet, i is the current magnitude in the poling coil, $H_{ci}$ is the intrinsic coercivity, and $N_{turns}$ is a total number of turns of the poling coil.

22. The method of claim 13, wherein each of the pair of magnetic tines comprises a blade, and the magnetic flexure comprises a sinusoidal shape.

23. The method of claim 22, wherein the blade comprises a plurality of teeth.

24. The method of claim 13, wherein the magnetic tine assembly comprises a magnetic stainless steel alloy.

25. A drilling fluid sensor array, comprising:

at least a portion of a flow conduit configured to circulate a drilling fluid comprising metallic swarf from a wellbore;

a first metallic swarf sensor coupled to the flow conduit, the first metallic swarf sensor comprising:

a first housing coupled to the flow conduit;

a first magnetic tine assembly that comprises a first pair of magnetic tines that extend from the housing and connect through a first magnetic flexure;

a first magnetic assembly at least partially enclosed within the first housing and coupled to the first magnetic tine assembly, the first magnetic assembly configured to magnetize the first magnetic tine assembly; and a first piezoelectric actuator at least partially enclosed within the first housing and coupled to the first magnetic tine assembly, the first piezoelectric actuator configured to resonate the first magnetic tine assembly at a variable resonance frequency; and a second metallic swarf sensor coupled to the flow conduit, the second metallic swarf sensor comprising:

a second housing coupled to the flow conduit;

a second magnetic tine assembly that comprises a second pair of magnetic tines that extend from the housing and connect through a second magnetic flexure;

a second magnetic assembly at least partially enclosed within the second housing and coupled to the second magnetic tine assembly, the second magnetic assembly configured to magnetize the second magnetic tine assembly; and a second piezoelectric actuator at least partially enclosed within the second housing and coupled to the second magnetic tine assembly, the second piezoelectric actuator configured to resonate the second magnetic tine assembly at a variable resonance frequency.

26. The drilling fluid sensor array of claim 25, wherein the first metallic swarf sensor is coupled to the flow conduit on a first side, and the second metallic swarf sensor is coupled to the flow conduit on a second side opposite the first side.

27. The drilling fluid sensor array of claim 26, comprising:

a third metallic swarf sensor coupled to the flow conduit, the third metallic swarf sensor comprising:

a third housing coupled to the flow conduit;

a third magnetic tine assembly that comprises a third pair of magnetic tines that extend from the housing and connect through a third magnetic flexure;

a third magnetic assembly at least partially enclosed within the third housing and coupled to the third magnetic tine assembly, the third magnetic assembly configured to magnetize the third magnetic tine assembly; and a third piezoelectric actuator at least partially enclosed within the third housing and coupled to the third magnetic tine assembly, the third piezoelectric actuator configured to resonate the third magnetic tine assembly at a variable resonance frequency; and a fourth metallic swarf sensor coupled to the flow conduit, the fourth metallic swarf sensor comprising:

a fourth housing coupled to the flow conduit;

a fourth magnetic tine assembly that comprises a fourth pair of magnetic tines that extend from the housing and connect through a fourth magnetic flexure;

a fourth magnetic assembly at least partially enclosed within the fourth housing and coupled to the fourth magnetic tine assembly, the fourth magnetic assembly configured to magnetize the fourth magnetic tine assembly; and a fourth piezoelectric actuator at least partially enclosed within the fourth housing and coupled to the fourth magnetic tine assembly, the fourth piezoelectric actuator configured to resonate the fourth magnetic tine assembly at a variable resonance frequency.

28. The drilling fluid sensor array of claim 27, wherein the third metallic swarf sensor is coupled to the flow conduit on the first side, and the fourth metallic swarf sensor is coupled to the flow conduit on the second side.

29. The drilling fluid sensor array of claim 25, wherein each of the first pair of magnetic tines comprises a blade, and the first magnetic flexure comprises a sinusoidal shape, and each of the second pair of magnetic tines comprises a blade, and the second magnetic flexure comprises the sinusoidal shape.

30. The drilling fluid sensor array of claim 29, wherein the blade of each magnetic tine of the first and second pair of magnetic tines comprises a flat side angled relative to a direction of flow of the drilling fluid.

\* \* \* \* \*